(12) United States Patent
Kirkland et al.

(10) Patent No.: US 8,962,266 B2
(45) Date of Patent: Feb. 24, 2015

(54) METHODS FOR ASSAYING ENZYME ACTIVITIES

(71) Applicant: Promega Corporation, Madison, WI (US)

(72) Inventors: Thomas Kirkland, Atascadero, CA (US); Andrew L. Niles, Madison, WI (US); Martha O'Brien, Madison, WI (US); Carolyn Woodroofe Hitko, Grover Beach, CA (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 14/090,728

(22) Filed: Nov. 26, 2013

(65) Prior Publication Data

US 2014/0099655 A1    Apr. 10, 2014

Related U.S. Application Data

(62) Division of application No. 13/228,791, filed on Sep. 9, 2011, now Pat. No. 8,632,992.

(60) Provisional application No. 61/381,675, filed on Sep. 10, 2010.

(51) Int. Cl.
| | |
|---|---|
| G01N 33/573 | (2006.01) |
| C12Q 1/00 | (2006.01) |
| G01N 33/53 | (2006.01) |
| C12Q 1/34 | (2006.01) |
| C07D 417/04 | (2006.01) |
| C07K 5/083 | (2006.01) |
| C07K 5/11 | (2006.01) |
| C07K 7/06 | (2006.01) |
| C12Q 1/48 | (2006.01) |

(52) U.S. Cl.
CPC ............. *C12Q 1/34* (2013.01); *C07D 417/04* (2013.01); *C07K 5/0806* (2013.01); *C07K 5/1019* (2013.01); *C07K 7/06* (2013.01); *C12Q 1/48* (2013.01)
USPC ............................... 435/7.4; 435/4; 435/7.72

(58) Field of Classification Search
CPC ..................................... C12Q 1/34; C12Q 1/48
See application file for complete search history.

(56) References Cited

U.S. PATENT DOCUMENTS

| | | | |
|---|---|---|---|
| 7,033,778 B2 | 4/2006 | Tamai et al. | |
| 8,632,992 B2 | 1/2014 | Kirkland et al. | |
| 2011/0046157 A1 | 2/2011 | Blackburn et al. | |

FOREIGN PATENT DOCUMENTS

| | | | |
|---|---|---|---|
| JP | 2003221398 | | 8/2003 |
| JP | 2003221398 A | * | 8/2003 |
| WO | WO 2012/033993 | | 5/2012 |

OTHER PUBLICATIONS

Aherne et al., "Assays for the identification and evaluation of histone acetyltranseferase inhibitors" Methods 26, 245-253 (2002).
Bodanszky et al., "Peptide Synthesis," John Wiley & Sons, 2d Ed., (1976).
Bolden et al., "Anticancer activities of histone deacetylase inhibitors" Nat. Rev. Drug Discovery, 5, 769-784 (2006).
Choudhary et al., "Lysine Acetylation Targets Protein Complexes and Co-Regulates Major Cellular Functions" Science, 325, 834-840 (2009).
Covington III, et al., "Antidepressant Actions of Histone Deacetylase Inhibitors" J. Neuroscience, 29, 11451-11460 (2009).
Gallinari et al., "HDACs, histone deacetylation and gene transcription: from molecular bilogy to cancer therapeutics" Cell Research, 17, 195-211 (2007).
Grozinger et al., "Deacetylase Enzymes: Biological Functions and the Use of Small-Molecule Inhibitors" Chem. Biol. 9, 3-16 (2002).
Heltweg et al., "In vitro assays for the determination of histone deacetylase activity" Methods, 36, 332-337 (2005).
Kouzarides, "Acetylation: a regulatory modification to rival phosphorylation?" EMBO, 19, 1176-1179 (2000).
Merrifield, "Solid Phase Peptide Synthesis. I. The Synthesis of a Tetrapeptide" 1963, J. Am. Chem. Soc. 85:2149-2154.
Monsees et al., "Synthesis and Characterization of a Bioluminogenic Substrate for alpha-Chymotrypsin." Anal. Biochem. vol. 221, 329-334 (1994).
Stuart and Young, "Solid Phase Peptide." Synthesis, Pierce Chemical Company, Rockford, 111, (1984).
T. W. Greene and P. G. M. Wuts, "Protecting Groups in Organic Synthesis" 3rd edition, John Wiley & Sons, 1999.
Finn and Hoffman, "The Synthesis of Peptides by Solution Methods with Emphasis on Peptide Hormones," vol. II, 3d Ed., Neurath et. al., Eds., p. 105-237, Academic Press, New York, N.Y. (1976).
Witt et al., "HDAC family: What are the cancer relevant targets?" Cancer Lett., 277, 8-21 (2009).
Wu et al., "Fluorescent reporters of the histone acetyltransferase" Analytical Biochemistry. 2008. vol. 380, 106-110.
Yamamoto et al., "Sirtuin Functions in Health and Disease" Mol. Endocrin., 21, 1745-1755 (2007).
PCT/US2011/050954 Partial International Search Report dated Nov. 16, 2011 (2 pages).
PCT/US2011/050954 International Search Report and Written Opinion dated Mar. 23, 2012 (17 pages).
United Stated Patent Office Action for U.S. Appl. No. 13/228,791 dated Jan. 28, 2013 (7 pages).
European Patent Office Comments on Written Opinion for Application No. 11763816.3 dated Apr. 25, 2013 (2 pages).
United Stated Patent Office Notice of Allowance for U.S. Appl. No. 13/228,791 dated Jul. 15, 2013 (10 pages).
United Stated Patent Office Notice of Allowance for U.S. Appl. No. 13/228,791 dated Aug. 22, 2013 (8 pages).

* cited by examiner

*Primary Examiner* — Suzanne M Noakes
*Assistant Examiner* — Jae W Lee
(74) *Attorney, Agent, or Firm* — Michael Best & Friedrich LLP

(57) ABSTRACT

The present invention provides compounds and methods for assaying activities of enzymes such as histone deacetylases and histone acetyltransferases. In some embodiments, the methods may be performed in one step. The compounds described herein features peptide-based compounds having at least one blocked lysine or arginine residue which are coupled to reporter moieties. The methods described herein involve reacting a compound described herein with an enzyme, such as a histone deacetylase enzyme or a histone acetyltransferase enzyme, and an endopeptidase that recognizes basic amino acids to release the reporter moiety which may be subsequently detected.

13 Claims, 2 Drawing Sheets

SEQUENCE LISTING

```
<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: Carbobenzyloxy (Cbz) group attached to Gln
<220> FEATURE:
<221> NAME/KEY: MISC_FEATURE
<222> LOCATION: (3)..(3)
<223> OTHER INFORMATION: 2 methyl groups (Me2) attached to Lys
<220> FEATURE:
<221> NAME/KEY: MISC_FEATURE
<222> LOCATION: (4)..(4)
<223> OTHER INFORMATION: Acetyl (Ac) group and aminoluciferin attached
      to Lys

<400> SEQUENCE: 1

Gln Pro Lys Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Carbobenzyloxy (Cbz) group attached to Gln
<220> FEATURE:
<221> NAME/KEY: MISC_FEATURE
<222> LOCATION: (3)..(3)
<223> OTHER INFORMATION: 2 methyl groups (Me2) attached to Lys
<220> FEATURE:
<221> NAME/KEY: MISC_FEATURE
<222> LOCATION: (4)..(4)
<223> OTHER INFORMATION: Aminoluciferin attached to Lys

<400> SEQUENCE: 2

Gln Pro Lys Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Carbobenzyloxy (Cbz) group and Trt group
      attached to Gln
<220> FEATURE:
<221> NAME/KEY: MISC_FEATURE
<222> LOCATION: (3)..(3)
<223> OTHER INFORMATION: 2 methyl groups (Me2) attached to Lys
<220> FEATURE:
<221> NAME/KEY: MISC_FEATURE
<222> LOCATION: (4)..(4)
<223> OTHER INFORMATION: Acetyl (Ac) group and aminocyanobenzothiazole
      group attached to Lys

<400> SEQUENCE: 3

Gln Pro Lys Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Carbobenzyloxy (Cbz) group attached to Gln
<220> FEATURE:
<221> NAME/KEY: MISC_FEATURE
<222> LOCATION: (3)..(3)
<223> OTHER INFORMATION: 2 methyl groups (Me2) attached to Lys
<220> FEATURE:
<221> NAME/KEY: MISC_FEATURE
<222> LOCATION: (4)..(4)
<223> OTHER INFORMATION: Acetyl (Ac) group and aminocyanobenzothiazole
      group attached to Lys

<400> SEQUENCE: 4

Gln Pro Lys Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Carbobenzyloxy (Cbz) group attached to Gln
<220> FEATURE:
<221> NAME/KEY: MISC_FEATURE
<222> LOCATION: (3)..(3)
<223> OTHER INFORMATION: 2 methyl groups (Me2) attached to Lys
<220> FEATURE:
<221> NAME/KEY: MISC_FEATURE
<222> LOCATION: (4)..(4)
<223> OTHER INFORMATION: TFA group and aminoluciferin attached to Lys

<400> SEQUENCE: 5

Gln Pro Lys Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 9-fluorenylmethyloxycarbonyl (Fmoc) group and
      methyl (Me) group attached to Arg
<220> FEATURE:
<221> NAME/KEY: MISC_FEATURE
<222> LOCATION: (3)..(3)
<223> OTHER INFORMATION: Acetyl (Ac) group attached to Lys
<220> FEATURE:
<221> NAME/KEY: MISC_FEATURE
<222> LOCATION: (4)..(4)
<223> OTHER INFORMATION: Acetyl (Ac) group and aminoluciferin attached
      to Lys

<400> SEQUENCE: 6

Arg His Lys Lys
1

<210> SEQ ID NO 7
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: 9-fluorenylmethyloxycarbonyl (Fmoc) group and 2
      methyl (Me2) groups attached to Lys
<220> FEATURE:
<221> NAME/KEY: MISC_FEATURE
<222> LOCATION: (5)..(5)
<223> OTHER INFORMATION: Acetyl (Ac) group and aminoluciferin attached
      to Lys

<400> SEQUENCE: 7

Lys Gly Gly Ala Lys
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 9-fluorenylmethyloxycarbonyl (Fmoc) group and 2
      methyl groups attached to Lys
<220> FEATURE:
<221> NAME/KEY: MISC_FEATURE
<222> LOCATION: (4)..(4)
<223> OTHER INFORMATION: Hydroxyl (OH) group attached to Ala

<400> SEQUENCE: 8

Lys Gly Gly Ala
1

<210> SEQ ID NO 9
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Boc group and 2 methyl (Me2) groups attached to
      Lys
<220> FEATURE:
<221> NAME/KEY: MISC_FEATURE
<222> LOCATION: (5)..(5)
<223> OTHER INFORMATION: Acetyl (Ac) group and aminoluciferin attached
      to Lys

<400> SEQUENCE: 9

Lys Gly Gly Ala Lys
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Boc group and 2 methyl (Me2) groups attached to
      Lys
<220> FEATURE:
<221> NAME/KEY: MISC_FEATURE
<222> LOCATION: (4)..(4)
<223> OTHER INFORMATION: Hydroxyl (OH) group attached to Ala

<400> SEQUENCE: 10

Lys Gly Gly Ala
1
```

-continued

```
<210> SEQ ID NO 11
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Boc group and 2 methyl (Me2) groups attached to
      Lys
<220> FEATURE:
<221> NAME/KEY: MISC_FEATURE
<222> LOCATION: (5)..(5)
<223> OTHER INFORMATION: TFA group and aminoluciferin attached to Lys

<400> SEQUENCE: 11

Lys Gly Gly Ala Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Carbobenzyloxy (Cbz) group attached to Ser
<220> FEATURE:
<221> NAME/KEY: MISC_FEATURE
<222> LOCATION: (2)..(2)
<223> OTHER INFORMATION: 2 methyl (Me2) groups attached to Lys
<220> FEATURE:
<221> NAME/KEY: MISC_FEATURE
<222> LOCATION: (7)..(7)
<223> OTHER INFORMATION: Acetyl (Ac) group and aminoluciferin attached
      to Lys

<400> SEQUENCE: 12

Ser Lys Glu Tyr Phe Ser Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Carbobenzyloxy (Cbz) group attached to Ser
<220> FEATURE:
<221> NAME/KEY: MISC_FEATURE
<222> LOCATION: (2)..(2)
<223> OTHER INFORMATION: 2 methyl (Me2) groups attached to Lys
<220> FEATURE:
<221> NAME/KEY: MISC_FEATURE
<222> LOCATION: (6)..(6)
<223> OTHER INFORMATION: Hydroxyl (OH) group attached to Ser

<400> SEQUENCE: 13

Ser Lys Glu Tyr Phe Ser
1               5

<210> SEQ ID NO 14
<211> LENGTH: 9
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Boc group and 2 methyl (Me2) groups attached to
      Lys
<220> FEATURE:
<221> NAME/KEY: MISC_FEATURE
<222> LOCATION: (5)..(5)
<223> OTHER INFORMATION: 2 methyl (Me2) groups attached to Lys
<220> FEATURE:
<221> NAME/KEY: MISC_FEATURE
<222> LOCATION: (9)..(9)
<223> OTHER INFORMATION: Acetyl (Ac) group and aminoluciferin attached
      to Lys

<400> SEQUENCE: 14

Lys Gly Leu Gly Lys Gly Gly Ala Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Boc group and 2 methyl (Me2) groups attached to
      Lys
<220> FEATURE:
<221> NAME/KEY: MISC_FEATURE
<222> LOCATION: (5)..(5)
<223> OTHER INFORMATION: 2 methyl (Me2) groups attached to Lys
<220> FEATURE:
<221> NAME/KEY: MISC_FEATURE
<222> LOCATION: (8)..(8)
<223> OTHER INFORMATION: Hydroxyl (OH) group attached to Ala

<400> SEQUENCE: 15

Lys Gly Leu Gly Lys Gly Gly Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Boc group and 2 methyl (Me2) groups attached to
      Lys
<220> FEATURE:
<221> NAME/KEY: MISC_FEATURE
<222> LOCATION: (5)..(5)
<223> OTHER INFORMATION: Aminoluciferin attached to Lys

<400> SEQUENCE: 16

Lys Gly Gly Ala Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Carbobenzyloxy (Cbz) group attached to Ser
<220> FEATURE:
<221> NAME/KEY: MISC_FEATURE
<222> LOCATION: (2)..(2)
<223> OTHER INFORMATION: 2 methyl (Me2) groups attached to Lys
<220> FEATURE:
<221> NAME/KEY: MISC_FEATURE
<222> LOCATION: (7)..(7)
<223> OTHER INFORMATION: Aminoluciferin attached to Lys

<400> SEQUENCE: 17

Ser Lys Glu Tyr Phe Ser Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Boc group and 2 methyl (Me2) groups attached to
      Lys
<220> FEATURE:
<221> NAME/KEY: MISC_FEATURE
<222> LOCATION: (5)..(5)
<223> OTHER INFORMATION: 2 methyl (Me2) groups attached to Lys
<220> FEATURE:
<221> NAME/KEY: MISC_FEATURE
<222> LOCATION: (9)..(9)
<223> OTHER INFORMATION: Aminoluciferin attached to Lys

<400> SEQUENCE: 18

Lys Gly Leu Gly Lys Gly Gly Ala Lys
1               5
```

METHODS FOR ASSAYING ENZYME ACTIVITIES

CROSS-REFERENCE TO RELATED APPLICATIONS

This application is a divisional of U.S. application Ser. No. 13/228,791, filed on Sep. 9, 2011, now U.S. Pat. No. 8,632,992, issued on Jan. 21, 2014, which claims priority to U.S. Provisional Application No. 61/381,675, filed on Sep. 10, 2010, the entire contents of which are hereby incorporated by reference.

INCORPORATION OF SEQUENCE LISTING

The instant application contains a Sequence Listing which has been submitted in text format via EFS-Web and is hereby incorporated by reference in its entirety. Said text copy, created on May 28, 2013, is named 13208490ASFILED_SequenceListing-Text and is 8,075 bytes in size.

BACKGROUND

In many assay technologies, it is necessary to use multiple enzymes to achieve an optimal assay. The goal of such an assay is to measure the activity of one enzyme (the target enzyme) on a substrate exclusively. However, once the target enzyme has catalyzed the reaction of interest, an additional enzyme or enzymes may be used to generate a signal that is easily quantifiable, can be measured in small amounts, or increases or decreases linearly with the activity of the enzyme.

An ideal assay would allow all substrates and enzymes to be combined in a single reaction mixture. However, additional enzymes must only react with the substrate of interest, and at the specified position on the substrate of interest, to prevent unwanted side reactions and allow the assay to monitor the activity of the target enzyme exclusively.

SUMMARY OF THE INVENTION

The present invention provides compounds and methods for assaying activities of enzymes such as histone deacetylases and histone acetyltransferases. In some embodiments, the assays may be performed in one step, i.e. a homogeneous assay.

Accordingly, in one aspect, the invention features a compound of formula (I):

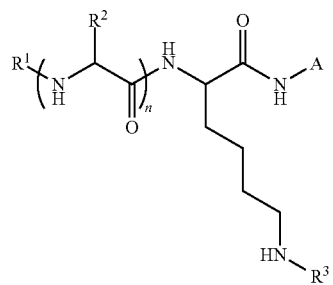

(I)

wherein:
A is a reporter moiety;
$R^1$ is selected from H, an amino protecting group and an amino blocking group;
n is an integer from 1 to 20;
each $R^2$ is independently an amino acid side chain, wherein at least one $R^2$ is selected from —$CH_2$—$CH_2$—$CH_2$—$CH_2$—$NR^{4a}R^{4b}$, —$CH_2$—$CH_2$—$CH_2$—$CH_2$—$N^+R^{4a}R^{4b}R^{4c}$ and —$CH_2$—$CH_2$—$CH_2$—$NH$—$C(=NR^{5a})NR^{5b}R^{5c}$;
$R^3$ is selected from acyl and sulfonyl;
each $R^{4a}$ is independently selected from hydrogen, alkyl and aryl;
each $R^{4b}$ is independently selected from alkyl and aryl;
each $R^{4c}$ is independently selected from hydrogen, alkyl and aryl;
each $R^{5a}$ is independently selected from hydrogen, alkyl and aryl;
each $R^{5b}$ is independently selected from alkyl and aryl; and
each $R^{5c}$ is independently selected from hydrogen, alkyl and aryl,
wherein when $R^2$ is —$CH_2$—$CH_2$—$CH_2$—$CH_2$—$N^+R^{4a}R^{4b}R^{4c}$, the compound further comprises a counteranion.

In another aspect, the invention features a method of detecting the activity of a histone deacetylase enzyme, comprising:
a) reacting a compound of formula (I) with a histone deacetylase enzyme and an endopeptidase that recognizes basic amino acids, under conditions sufficient to allow the histone deacetylase enzyme to react with the compound of formula (I) to form a product, and the endopeptidase to react with the product to release a compound A-$NH_2$; and
b) detecting the compound A-$NH_2$.

In another aspect, the invention features a compound of formula (II):

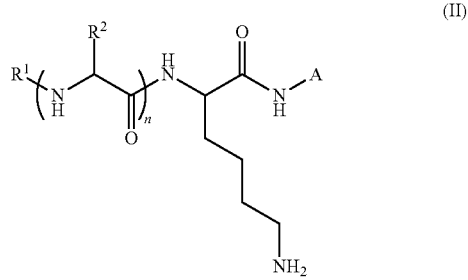

(II)

wherein:
A is a reporter moiety;
$R^1$ is selected from H, an amino protecting group and an amino blocking group;
n is an integer from 1 to 20;
each $R^2$ is independently an amino acid side chain, wherein at least one $R^2$ is selected from —$CH_2$—$CH_2$—$CH_2$—$CH_2$—$NR^{4a}R^{4b}$, —$CH_2$—$CH_2$—$CH_2$—$CH_2$—$N^+R^{4a}R^{4b}R^{4c}$ and —$CH_2$—$CH_2$—$CH_2$—$NH$—$C(=NR^{5a})NR^{5b}R^{5c}$;
each $R^{4a}$ is independently selected from hydrogen, alkyl and aryl;
each $R^{4b}$ is independently selected from alkyl and aryl;
each $R^{4c}$ is independently selected from hydrogen, alkyl and aryl;
each $R^{5a}$ is independently selected from hydrogen, alkyl and aryl;

each $R^{5b}$ is independently selected from alkyl and aryl; and
each $R^{5c}$ is independently selected from hydrogen, alkyl and aryl,
wherein when $R^2$ is —CH$_2$—CH$_2$—CH$_2$—CH$_2$—N$^+$R$^{4a}$R$^{4b}$R$^{4c}$, the compound further comprises a counteranion.

In another aspect, the invention features a method of detecting the activity of a histone acetyltransferase enzyme, comprising:

a) reacting a compound of formula (II) with a histone acetyltransferase enzyme under conditions sufficient to allow the histone acetyltransferase enzyme to react with the compound of formula (II) to form a product;

b) adding an endopeptidase that recognizes basic amino acids, such that the endopeptidase reacts with the compound of formula (II) to release a compound A-NH$_2$; and c) detecting the compound A-NH$_2$.

In another aspect, the invention features a composition comprising:

a. a compound of formula (I) or formula (II),
b. an endopeptidase that recognizes basic amino acids, and
c. optionally, a detection reagent.

In another aspect, the invention features a kit comprising:

a. a compound of formula (I) or formula (II),
b. an endopeptidase that recognizes basic amino acids, and
c. optionally, a detection reagent.

In another aspect, the invention features a method of detecting the activity of a target enzyme, comprising:

a) reacting a compound comprising at least one blocked arginine or lysine residue with a target enzyme and an endopeptidase that recognizes basic amino acids, wherein the reaction results in the formation of a compound A-NH$_2$; and b) detecting the compound A-NH$_2$.

Other aspects and embodiments of the invention will become apparent from the following description and accompanying figures.

DETAILED DESCRIPTION OF THE INVENTION

Figure 1:
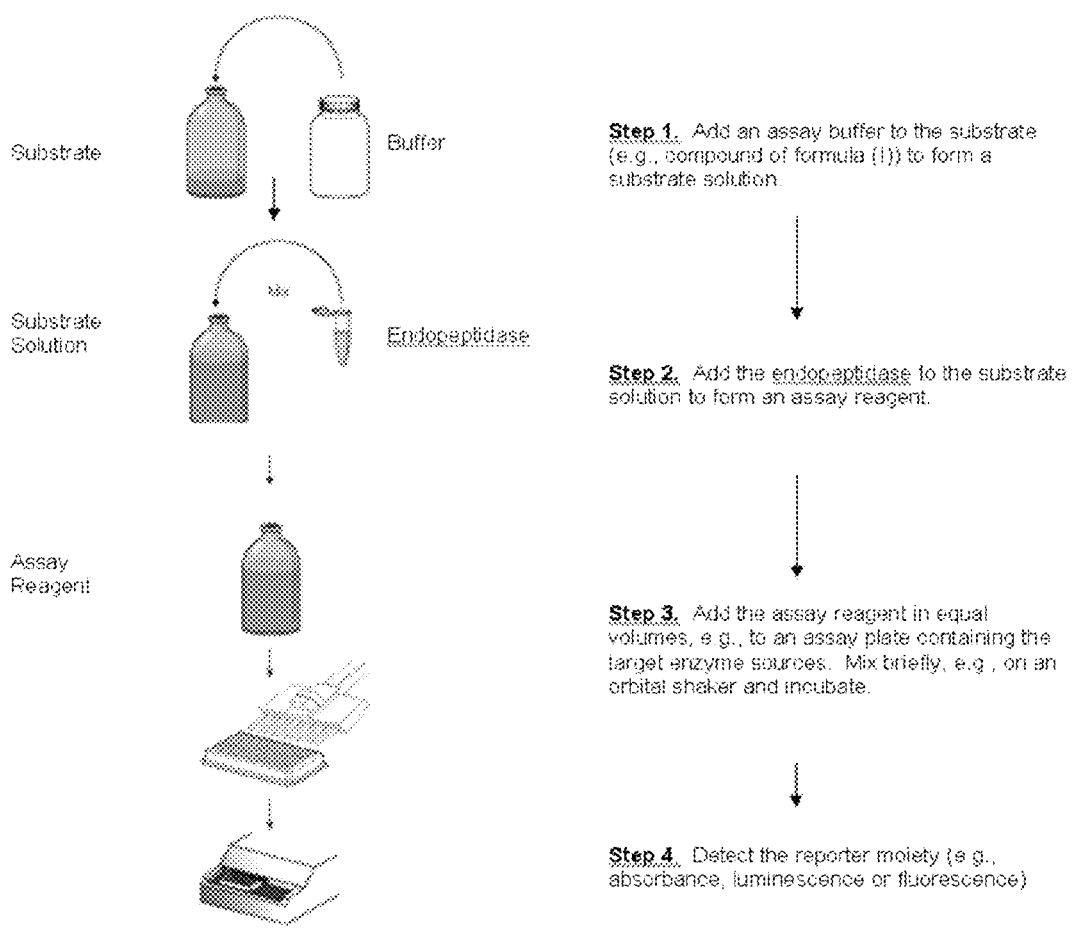
FIG. 1 is an illustration of an enzyme assay carried out using a method of the invention.

The present invention provides compounds and methods for assaying activities of enzymes such as histone deacetylases and histone acetyltransferases. In some embodiments, the assays can be performed in one step, i.e. a homogeneous assay. The compounds described herein are peptide-based and have at least one blocked lysine or arginine residue in the peptide chain. The peptide chains of these compounds are terminated with a potentially modified lysine residue that is directly coupled to a reporter moiety. This terminal lysine is the site of action of the enzyme to be measured, such as a histone deacetylase or histone acetyltransferase enzyme. The methods described herein involve reacting a compound described herein with an enzyme, such as a histone deacetylase or histone acetyltransferase, and an endopeptidase that recognizes basic amino acids, such as trypsin or Lys-C, to release the reporter moiety which may be subsequently detected.

Definitions

The term "acyl," as used herein, refers to a group of the formula —C(=O)R, wherein R is a substituent of an acyl group, for example, a $C_{1-7}$, $C_{1-6}$, $C_{1-5}$ or $C_{1-4}$ branched or unbranched alkyl group, such as a methyl, ethyl, propyl, butyl, pentyl, hexyl or heptyl group (also referred to as alkylacyl or alkanoyl groups); a $C_{3-20}$, $C_{3-10}$ or $C_{3-6}$ heterocyclyl group (also referred to as a heterocyclylacyl group), or a $C_{6-30}$, $C_{5-20}$ or $C_{6-14}$ aryl group (also referred to as arylacyl groups). Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl). R may be further substituted, for example, with one or more halo, oxo or hydroxy groups. For example, R may be haloalkyl such as trifluoromethyl.

As used herein, the term "alkyl" refers to a branched, unbranched, or cyclic hydrocarbon having, for example, from 1 to 30 carbon atoms, and often 1 to 12, 1 to 10, 1 to 8, 1 to 7, 1 to 6, 1 to 5 or 1 to 4 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms, for example from 6 to 20 carbon atoms or 6 to 14 carbon atoms. For example, the aryl group may be a $C_6$, $C_{10}$, $C_{12}$, $C_{13}$ or $C_{14}$ aryl group. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

As used herein, "halo" or "halogen" refers to fluorine, chlorine, bromine or iodine.

The term "sulfone" or "sulfonyl," as used herein, refers to a group of the formula —S(=O)$_2$R, wherein R is a substituent of a sulfone, for example, a $C_{1-12}$, $C_{1-10}$, $C_{1-8}$, $C_{1-7}$, $C_{1-6}$, $C_{1-5}$ or $C_{1-4}$ alkyl group, such as a methyl, ethyl, propyl, butyl, pentyl, hexyl or heptyl group; a $C_{3-20}$, $C_{3-10}$ or $C_{3-6}$ heterocyclyl group; or a $C_{6-30}$, $C_{5-20}$ or $C_{6-14}$ aryl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenylsulfonyl (nosyl).

The term "counteranion," as used herein, refers to an atom or group having a formal negative charge that is present to balance the charge of a positively charged amino acid side chain. Counteranions include, but are not limited to, halides (e.g., fluoride, chloride, bromide and iodide), $N_3^-$, $PO_4^{3-}$, $HPO_4^{2-}$, $H_2PO_4^-$, $SO_4^{2-}$, $HSO_4^-$, $NO_3^-$, $ClO_4^-$, $CO_3^{2-}$, $HCO_3^-$, $CrO_4^{2-}$, $Cr_2O_7^{2-}$, $CN^-$, $OH^-$, $C_2O_4^{2-}$, $MnO_4^-$, $BF_4^-$, $PF_6^-$, $HCOO^-$, $CH_3COO^-$, $CF_3COO^-$, and the like.

The term "natural amino acid" as used herein refers to any one of the common, naturally occurring L-amino acids found in proteins, including glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid" as used herein refers to all amino acids which are not natural amino acids as described above. Such amino acids include the D-isomers of any of the 20 naturally occurring amino acids described above. Unnatural amino acids also include homoserine, ornithine, norleucine, and thyroxine. Additional unnatural amino acids are well known to one of ordinary skill in the art. An unnatural amino acid may be a D- or L-isomer. An unnatural amino acid may also be an alpha amino acid or a beta amino acid. An unnatural amino acid may also be a post-translationally modified amino acid, such as a phosphorylated serine, threonine or tyrosine, an acylated lysine, or an alkylated lysine or arginine. Many forms of post-translationally modified amino acids are known.

The term "protected amino acid," as used herein, refers to an amino acid side chain as described above which additionally contains a protected functional group. Protecting groups are well known in the art and are intended to protect such functional groups as amino, hydroxy, thio or carboxy against undesirable reactions during synthetic procedures. The protecting groups may be removed by a chemical reaction following the synthesis. Examples of protected amino acid side chains include benzyloxymethyl derived from serine, (4-methoxyphenyl)methyl derived from tyrosine, and tert-butylpropanoate derived from glutamate.

More generally, the term "amino acid," as used herein, encompasses natural amino acids, unnatural amino acids and protected amino acids.

The term "amino acid side chain," as used herein, refers to the group attached to the a-carbon of an amino acid. It is the characterizing portion of an amino acid and is derived from a corresponding amino acid by elimination of the $NH_2CHC(O)OH$ moiety. For example, the amino acid side chain of alanine is methyl, and the amino acid side chain of phenylalanine is phenylmethyl. An amino acid side chain may be a natural amino acid side chain or an unnatural amino acid side chain. In some embodiments, an amino acid side chain may be a protected amino acid side chain.

An "amino protecting group," as used herein, refers to a moiety that prevents chemical reactions from occurring on the nitrogen atom to which that protecting group is attached. An amino protecting group must also be removable by a chemical reaction. Such groups are well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Suitable amino protecting groups include, but are not limited to, carbobenzyloxy (—NHCO—OCH$_2$C$_6$H$_5$ or —NH-Cbz); t-butyloxycarbonyl (—NHCO—OC(CH$_3$)$_3$ or —NH-Boc); 9-fluorenylmethyloxycarbonyl (—NH-Fmoc), 2,2,2-trichloroethyloxycarbonyl (—NH-Troc), and allyloxycarbonyl (—NH-Alloc). (In each of the above, the —NH— represents the nitrogen from the amino group that is being protected.)

An "amino blocking group," as used herein, refers to a moiety that prevents chemical reactions from occurring on the nitrogen atom to which that blocking group is attached. In contrast to an amino protecting group, an amino blocking group is not intended to be removed by a chemical reaction. Such groups include, for example, acyl groups such as acetyl (—NHCO—CH$_3$), and succinyl (—NH—CO—CH$_2$—CH$_2$—COO$^-$). (In each of the above, the —NH— represents the nitrogen from the amino group that is being blocked.)

As used herein, the term "aminoluciferin" refers to (4S)-2-(6-amino-1,3-benzothiazol-2-yl)-4,5-dihydrothiazole-4-carboxylic acid, or a substituted analog of this molecule.

It is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

Also, it is to be understood that the phraseology and terminology used herein is for the purpose of description and should not be regarded as limiting. The use of "comprising," "including," "having," and variations thereof herein is meant to encompass the items listed thereafter and equivalents thereof as well as additional items.

Histone Deacetylases and Histone Acetyltransferases

Histones are proteins found in eukaryotic cell nuclei and are involved in the packaging and ordering of DNA into structural units called nucleosomes. They are the chief protein components of chromatin acting as spools around which DNA winds. Histone tails are normally positively charged due to the protonation of amine groups on lysine and arginine amino acids. These positive charges help the histone tails to interact with and bind to the negatively charged phosphate groups on the DNA backbone. Acetylation of the ε-amino groups of lysine residues, effected by histone acetyltransferases (HATs), converts the amino groups to amides, eliminating the positive charge thereby lowering the affinity for DNA. The decreased affinity allows chromatin expansion, permitting genetic transcription of the DNA to take place. Histone deacetylases (HDACs) remove the acetyl groups from the lysine residues on the histones, increasing the positive charge of histone tails and encouraging binding between histones and the DNA backbone. The increased DNA binding condenses DNA structure and prevents transcription. Histone acetylation and deacetylation therefore play an important role in the regulation of gene expression (*Cell Research*, 17, 195-211 (2007)). In addition to the role HATs and HDACs play in modifying histones, they have also been found to acetylate and deacetylate a broad array of other proteins (*Science*, 325, 834-840 (2009)). Acetylation has been said to rival phosphorylation in terms of its relevance in cellular biochemistry (*EMBO*, 19, 1176-1179 (2000)).

HDACs are classified into four groups based on their function, DNA sequence similarity, and homology to yeast histone deacetylases (*Chem. Biol.* 9, 3-16 (2002)):

Class I, which includes HDAC1, -2, -3 and -8, are related to yeast RPD3 gene.

Class II, which includes HDAC4, -5, -6, -7, -9 and -10, are related to yeast Hda1 gene.

Class III, also known as the sirtuins, are related to the Sir2 gene and include SIRT1-7.

Class IV, which includes HDAC11, has features of both Class I and II.

Classes I and II are considered "classical" HDACs whose activities are inhibited by trichostatin A (TSA) by binding to the zinc-containing catalytic domain. Class III is a family of NAD$^+$-dependent proteins not affected by TSA. Class IV is a hybrid category based on DNA sequence similarity to those in Classes I and II.

HDACs have been recognized as potentially useful therapeutic targets for a broad range of human disorders (*Nat. Rev. Drug Discovery*, 5, 769-784 (2006); *J. Neuroscience*, 29, 11451-11460 (2009)). HDAC inhibitors are being developed for cancer therapy as some have been found to inhibit cell proliferation and induce differentiation and/or apoptosis of tumor cells (*Cancer Lett.*, 277, 8-21 (2009)). HDACs may also play a role in diabetes and other metabolic disorders as well as age-related disorders (*Mol. Endocrin.*, 21, 1745-1755 (2007)).

Thus, assays for HDAC activity are highly desirable, not only as research tools to aid in the continuing characterization of the biological relationships between the different classes, but also to aid in the development of new HDAC inhibitors (*Methods*, 36, 332-337 (2005)). Similarly, assays for HAT activity are also desirable (*Methods* 26, 245-253 (2002)).

Assays

An exemplary assay for HDAC activity is illustrated in Scheme 1. In substrate compound A, X is any amino acid, n is an integer from 1 to about 20, and R is hydrogen, an amino protecting group or an amino blocking group. The activity of the HDAC enzyme removes the acetyl group from compound A, generating compound B.

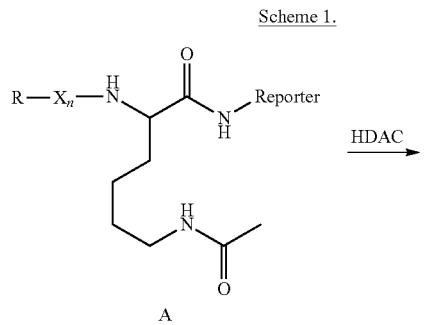

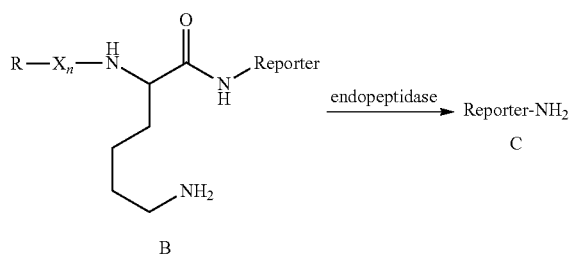

In order to generate a signal, the amide bond between the peptide and the reporter moiety must be cleaved to generate compound C, which can then be detected. In order to convert compound B into compound C, an endopeptidase that recognizes basic amino acids, such as trypsin, is added to the assay system. The specificity of the endopeptidase for unmodified lysine prevents it from cleaving compound A, and as a result, all of the signal generated in the assay is dependent on HDAC activity.

The reporter moiety can be chosen such that it does not produce a signal when it is still bound to the peptide. For example, a fluorophore may be quenched when bound to the peptide, but may be detectable when released. Another example of a suitable reporter moiety would be aminoluciferin, which is not a substrate for luciferase when bound to the peptide, but will react with luciferase to generate luminescence when released. The fluorescence or luminescence of compound C can be quantified to determine the amount of compound C present, which is then used to determine the activity of the target enzyme. The assay described above may be conducted entirely in one step, i.e. a homogeneous assay, so HDAC activity can be immediately detected.

To optimize the assays described above, additional amino acids $(X)_n$ in compound A can be incorporated. Optimization of this amino acid sequence may allow for better recognition of the substrate by the HDAC, improving the overall performance of the assay. Careful selection of the amino acids may also allow for selectivity between different HDAC isozymes. An assay that selectively detects the activity of one HDAC isozyme over another would be an extremely valuable research tool. However, the assay design illustrated in Scheme 1 precludes the use of lysine or arginine residues in the recognition sequence $(X)_n$, especially if the assay is to be performed in one-step. If an arginine or lysine were included, it could be recognized by an endopeptidase that recognizes basic amino acids, such as trypsin. Compound A could thus be cleaved prior to reaction with the HDAC enzyme, if the endopeptidase is included in the initial reaction mixture.

Inclusion of a lysine or arginine residue in this recognition sequence may be important to such recognition and selectivity. The compounds and methods of the present invention were therefore designed to allow for the use of lysine and arginine as amino acids in the recognition sequence $(X)_n$, while preventing recognition by an endopeptidase that recognizes basic amino acids. The compounds and methods use lysine or arginine residues that are modified to block recognition by the endopeptidase while still allowing recognition by the target enzyme. Therefore, the substrate will not be cleaved until acted upon by the target enzyme ensuring that any signal from the reporter moiety is due to the activity of the target enzyme, such as a HDAC. This allows the assay to be easily performed in one step.

Blocking groups that prevent lysine and arginine residues from being recognized by endopeptidases that recognize basic amino acids, such as trypsin, include alkyl groups and aryl groups. Alkylated or arylated lysine and arginine residues may be synthesized, or they may be purchased from commercial sources.

A specific exemplary assay using a modified lysine residue in the recognition sequence of a substrate is illustrated in Scheme 2. In this example, a dimethylated lysine residue is present in the recognition sequence. The presence of the methyl groups blocks recognition by the endopeptidase, such as trypsin, and thereby prevents cleavage between the dimethylated lysine and the acetylated lysine residues. The substrate D is deacetylated by the HDAC enzyme, producing product E. Trypsin recognizes the deacetylated lysine residue and cleaves the adjacent amide bond to release aminoluciferin F. Luciferase then reacts with F to produce a luminescent signal. Neither compound D nor compound E is recognized by luciferase.

Scheme 2.

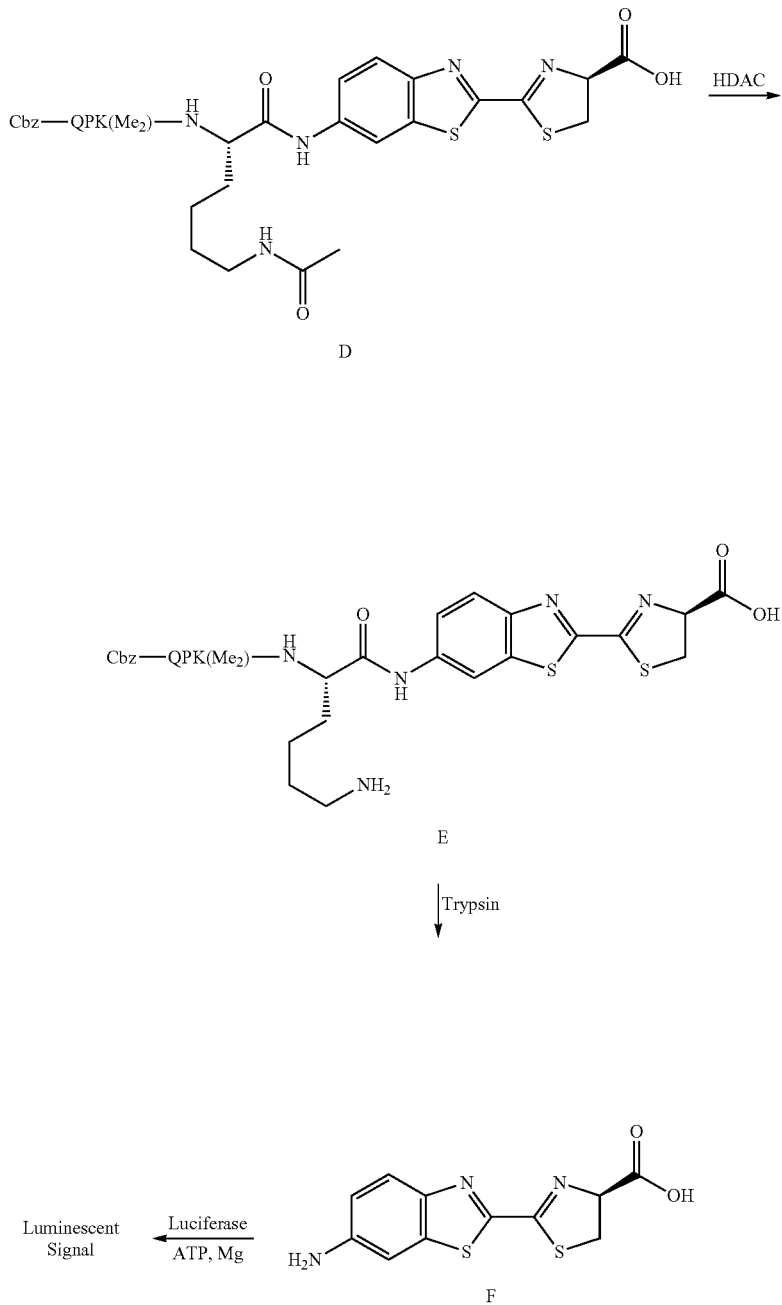

While the above assay can be performed in multiple steps, e.g., by first incubating substrate D with the HDAC, and then adding trypsin and luciferase in a subsequent step or steps to produce the luminescent signal, the assay can be performed in one step. The substrate D, the HDAC, trypsin, luciferase and any required cofactors can be combined in a single reaction mixture, which can result in a coupled, near-simultaneous reaction. The ability to perform the assay in one step leads to fast data acquisition, with a signal that may be proportional to the NAD-dependent deacetylase activity. A schematic illustrating a one-step reaction is illustrated in FIG. 1.

An exemplary assay for HAT activity is illustrated in Scheme 3. The variables are as defined above in Scheme 1. In this case, activity of the HAT leads to acetylation of the lysine residue of compound G to form compound H, which does not react with the endopeptidase. The substrate G is recognized by the endopeptidase to produce reporter compound I. Therefore, in this case, the HAT activity is monitored by the quantitative decrease in signal from the reporter. In this assay, compound G is first preincubated with the HAT (step 1), and the endopeptidase is added to the resulting mixture after the initial reaction (step 2). This ensures that the HAT and endopeptidase will not compete for compound G, and that all signal output from the reporter accurately reflects only the amount of G that is not converted to H by the HAT.

Scheme 3.

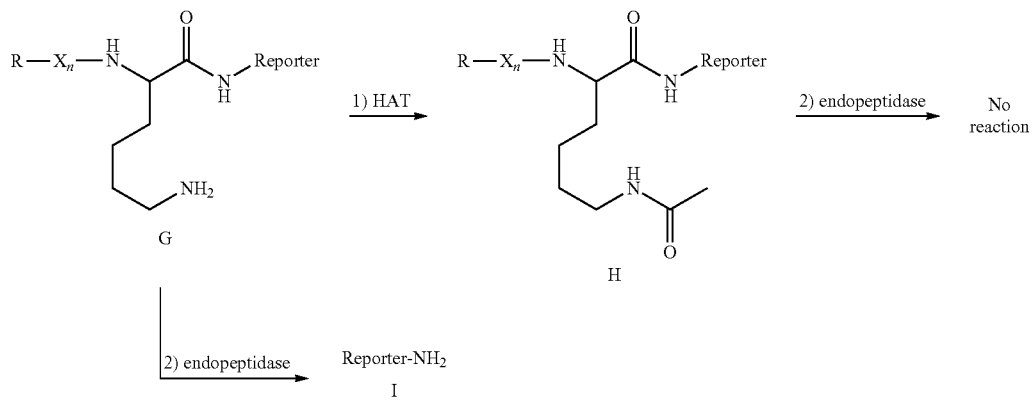

Use of blocked lysine and arginine residues in the recognition sequence $X_n$ allows for optimization of recognition by the HAT of interest, while preventing compound G from being cleaved by the endopeptidase at positions other than the C-terminal lysine that is conjugated to the reporter moiety. Potential advantages to the removal of endopeptidase cleavage sites in the recognition may include simplified kinetics of the coupled enzyme reaction, reduction of the quantity of endopeptidase required and reduction in the time required for cleavage of the peptide from the reporter.

Peptide Substrates

In one aspect, the invention features novel compounds that may be used in a homogenous assay, such as the assays described herein. The compounds feature at least one blocked (e.g., methylated, dimethylated or arylated) lysine or arginine residue which prevents recognition by an endopeptidase that recognizes basic amino acids.

In some embodiments, the compounds feature a C-terminal lysine residue that may be protected (e.g., arylated or sulfonylated) and conjugated to a reporter moiety. Such compounds may be used in assays to detect the activity of a target enzyme, e.g., a HDAC. For example, the acetylated lysine residue is recognized by a HDAC enzyme, which deacetylates the lysine residue to yield a product with lysine having its native free amino group. The product may be recognized and cleaved by the endopeptidase to release the reporter moiety, which may be subsequently detected. The activity of the HDAC enzyme can be calculated based on the amount of reporter moiety detected.

Exemplary peptide substrates of the invention include compounds of formula (I):

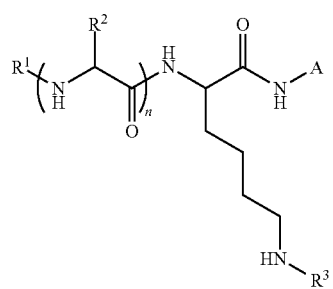

(I)

wherein:

A is a reporter moiety;

$R^1$ is selected from H, an amino protecting group and an amino blocking group;

n is an integer from 1 to 20;

each $R^2$ is independently an amino acid side chain, wherein at least one $R^2$ is selected from $-CH_2-CH_2-CH_2-CH_2-NR^{4a}R^{4b}$, $-CH_2-CH_2-CH_2-CH_2-N^+R^{4a}R^{4b}R^{4c}$ and $-CH_2-CH_2-CH_2-NH-C(=NR^{5a})NR^{5b}R^{5c}$;

$R^3$ is selected from acyl and sulfonyl;

each $R^{4a}$ is independently selected from hydrogen, alkyl and aryl;

each $R^{4b}$ is independently selected from alkyl and aryl;

each $R^{4c}$ is independently selected from hydrogen, alkyl and aryl;

each $R^{5a}$ is independently selected from hydrogen, alkyl and aryl;

each $R^{5b}$ is independently selected from alkyl and aryl; and each $R^{5c}$ is independently selected from hydrogen, alkyl and aryl, wherein when $R^2$ is $-CH_2-CH_2-CH_2-CH_2-N^+R^{4a}R^{4b}R^{4c}$, the compound further comprises a counteranion.

In some embodiments, A is selected from an aminoluciferin, a coumarin, a rhodamine, a coelenterazine, resorufin and cresyl violet.

In some embodiments, $R^1$ is an amino protecting group or an amino blocking group selected from the group consisting of 9-fluorenylmethyloxycarbonyl (Fmoc), carbobenzyloxy (Cbz), tertbutyloxy (Boc), acetyl and succinyl.

In some embodiments, n is 2, 3, 4 or 5.

In some embodiments, at least one $R^2$ is $-CH_2-CH_2-CH_2-CH_2-NR^{4a}R^{4b}$. In some embodiments, $R^{4a}$ is hydrogen and $R^{4b}$ is methyl. In some embodiments, $R^{4a}$ and $R^{4b}$ are each methyl.

In some embodiments, at least one $R^2$ is $-CH_2-CH_2-CH_2-CH_2-N^+R^{4a}R^{4b}R^{4c}$. In some embodiments, $R^{4a}$, $R^{4b}$ and $R^{4c}$ are each methyl.

In some embodiments, at least one $R^2$ is $-CH_2-CH_2-CH_2-NH-C(=NR^{5a})NR^{5b}R^{5c}$. In some embodiments, $R^{5a}$ and $R^{5b}$ are hydrogen and $R^{5c}$ is methyl.

In some embodiments, R³ is acyl (e.g., acetyl or trifluoroacetyl).
Exemplary compounds of the invention include the following:
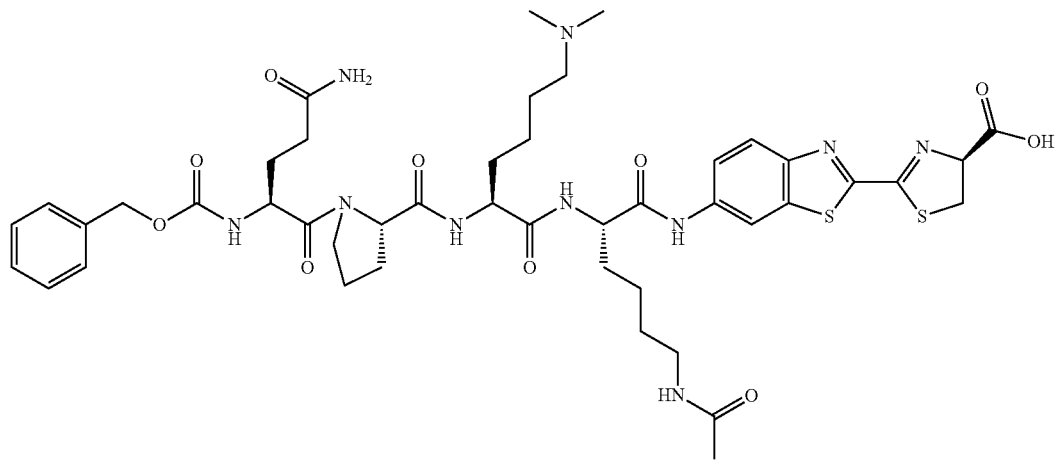
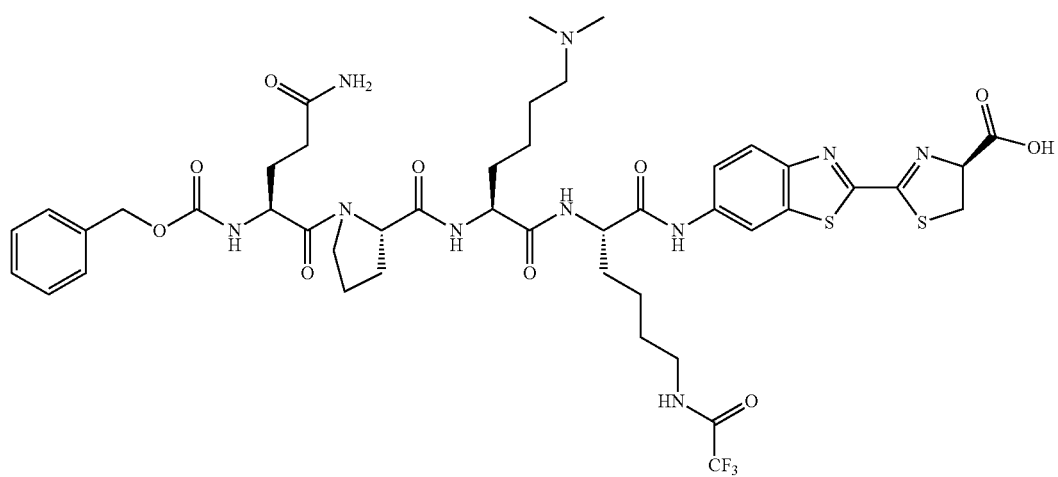
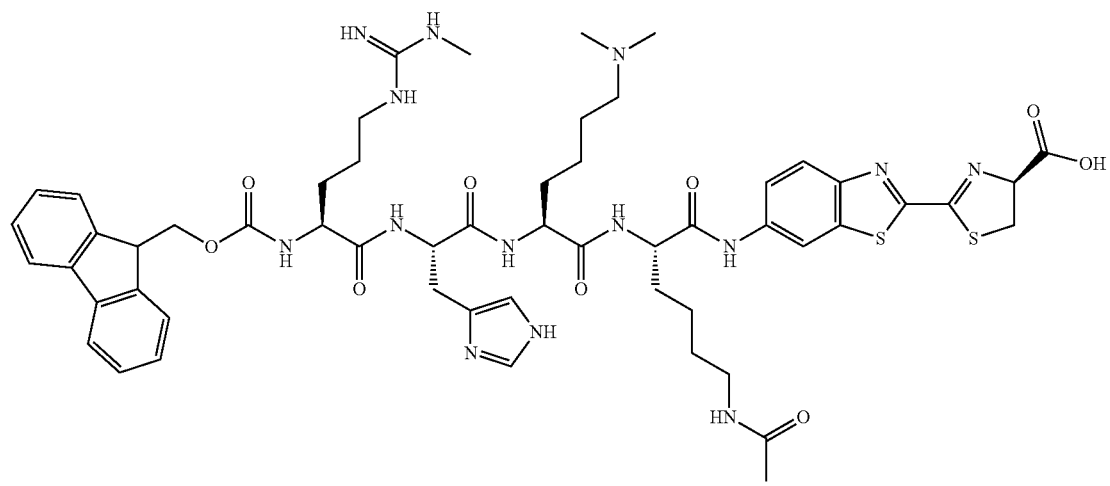

-continued
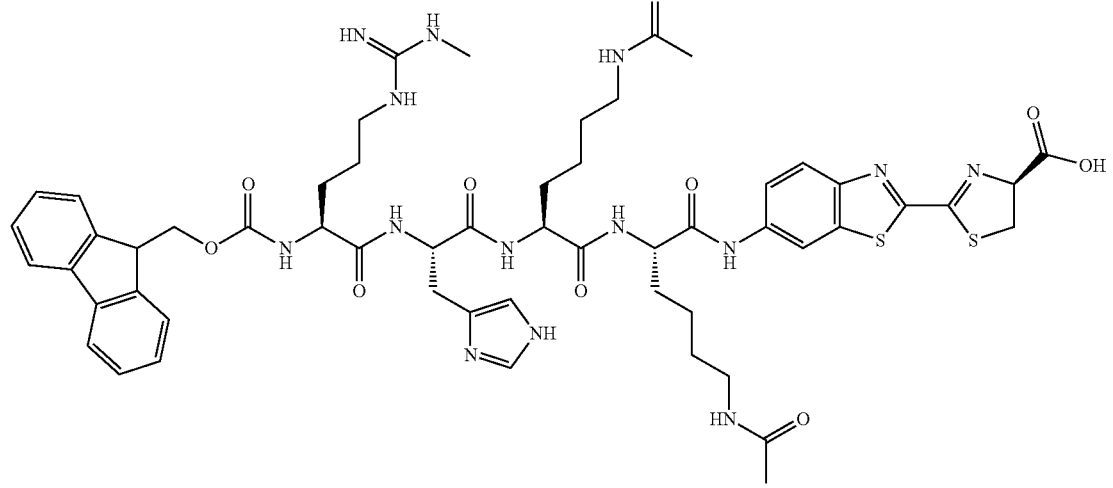
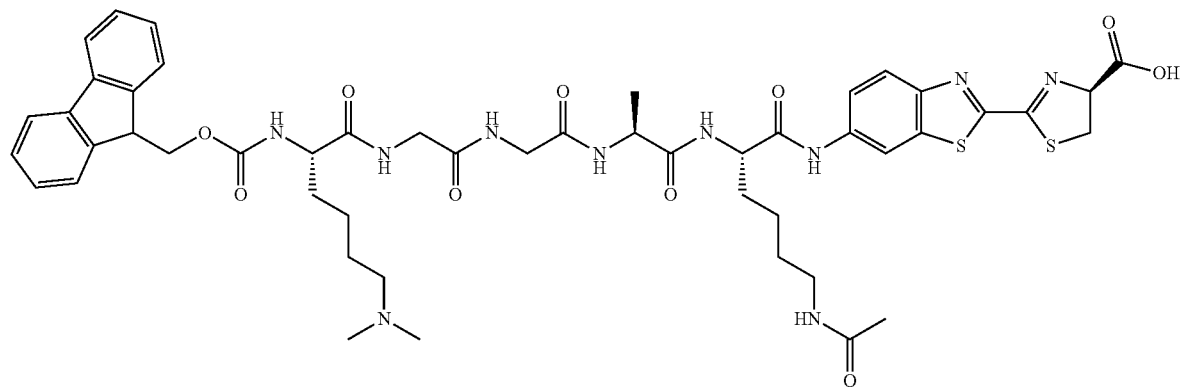
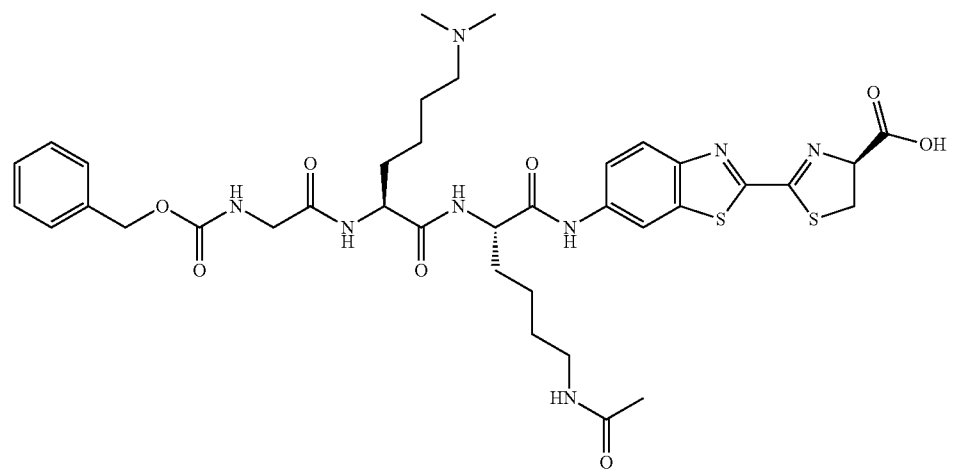

-continued
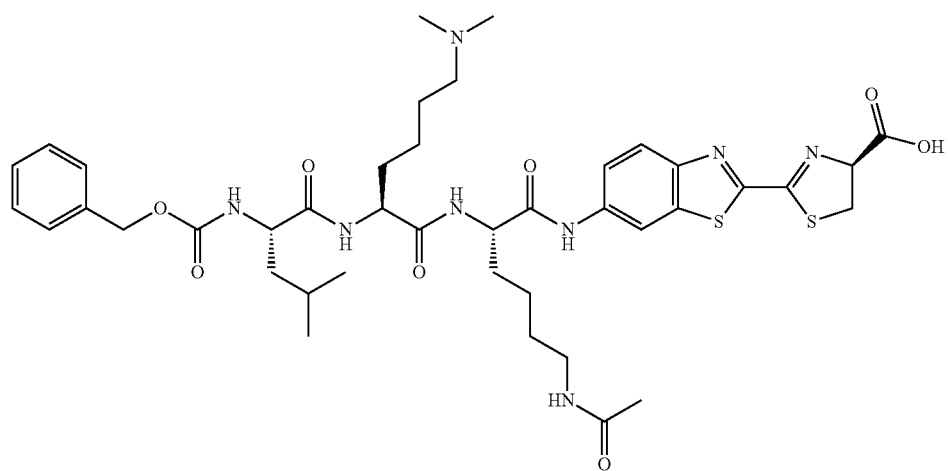
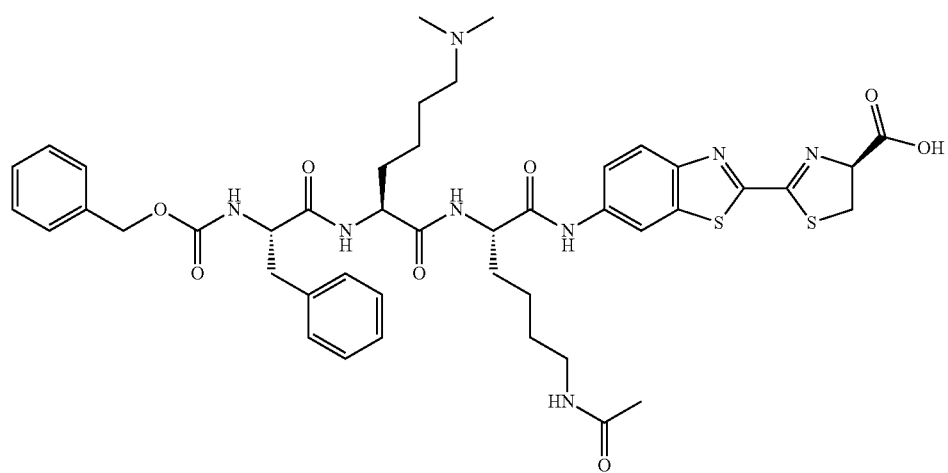
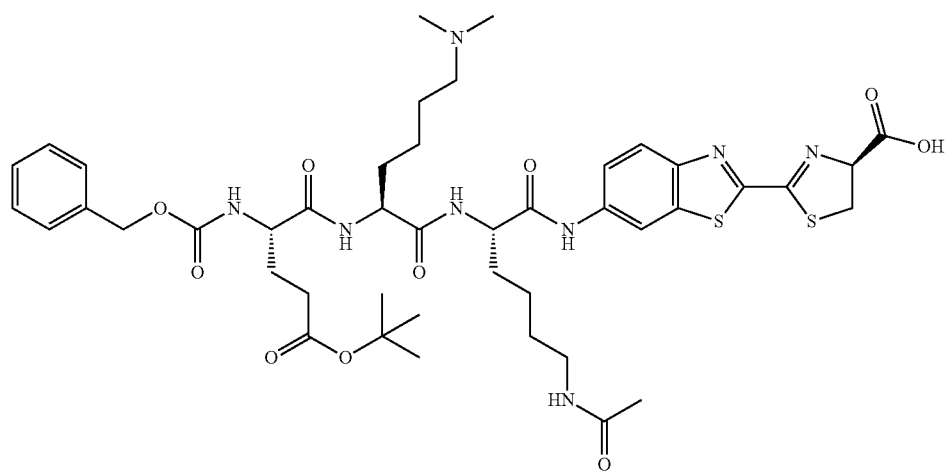

-continued
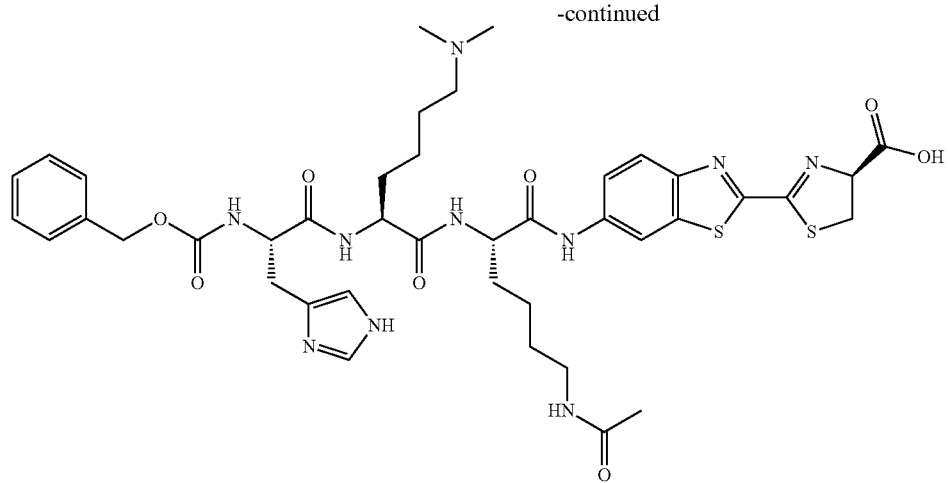
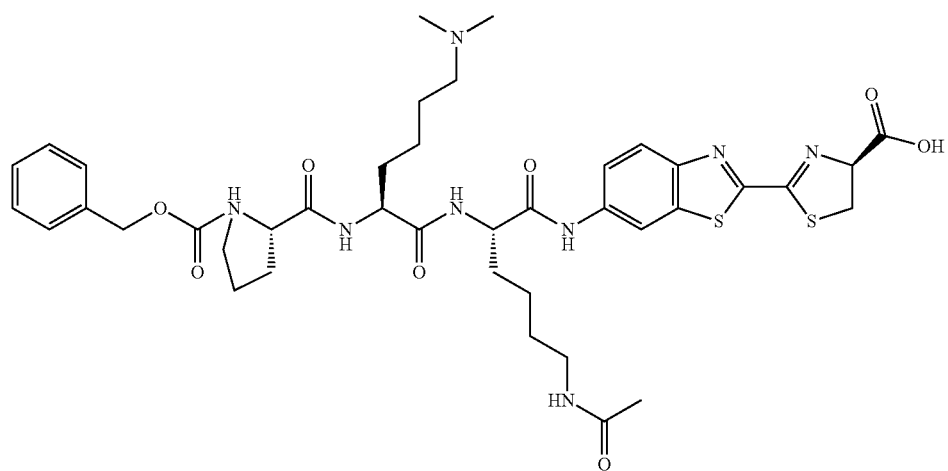
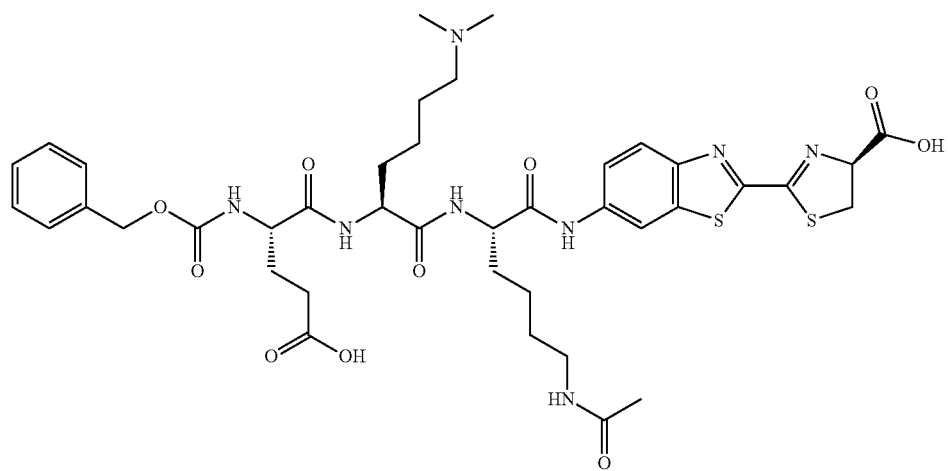

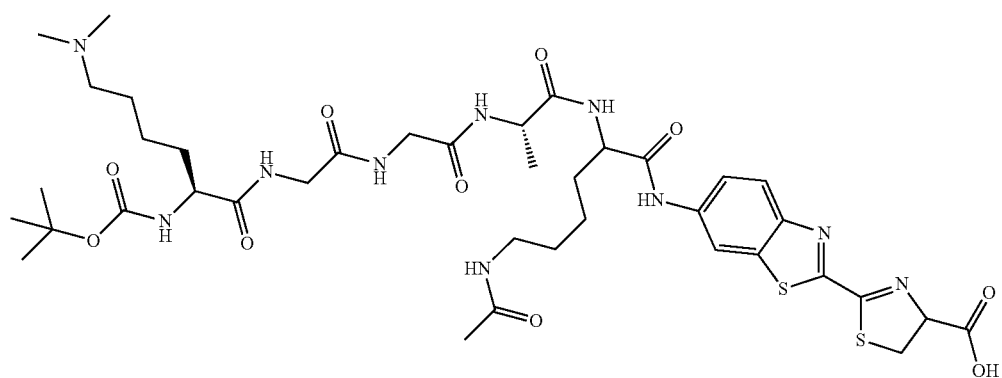
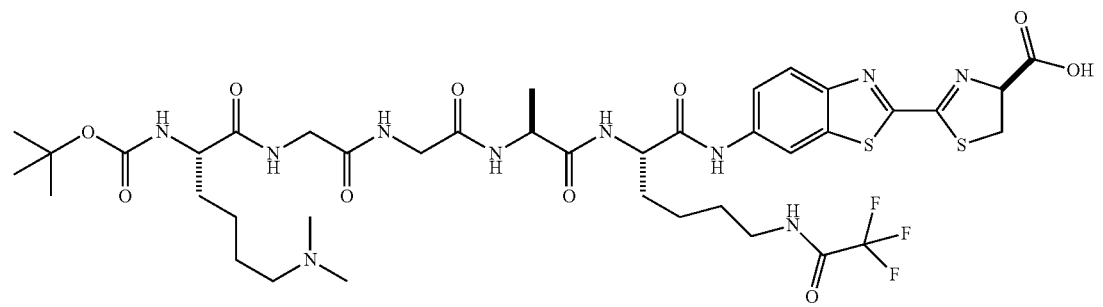
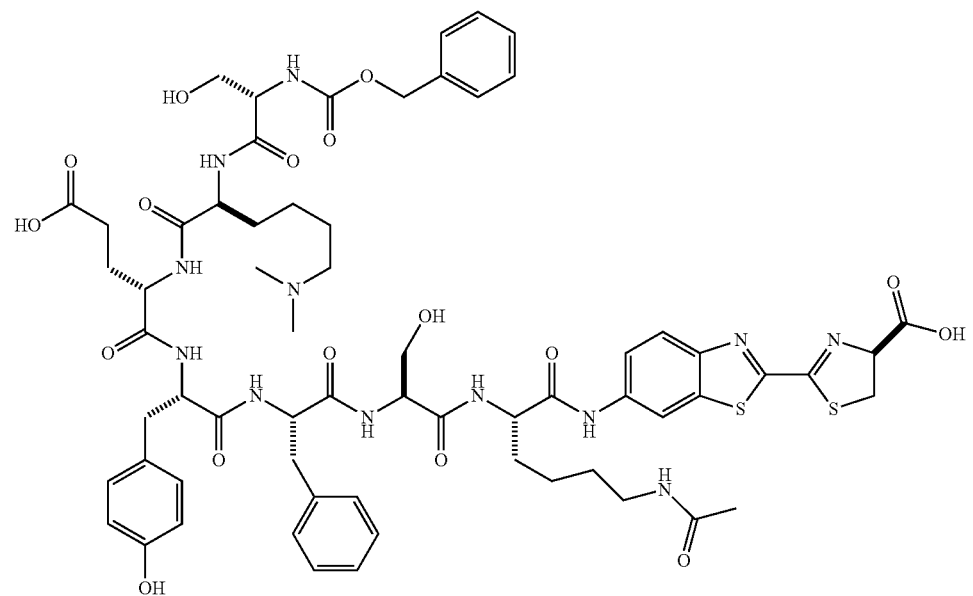

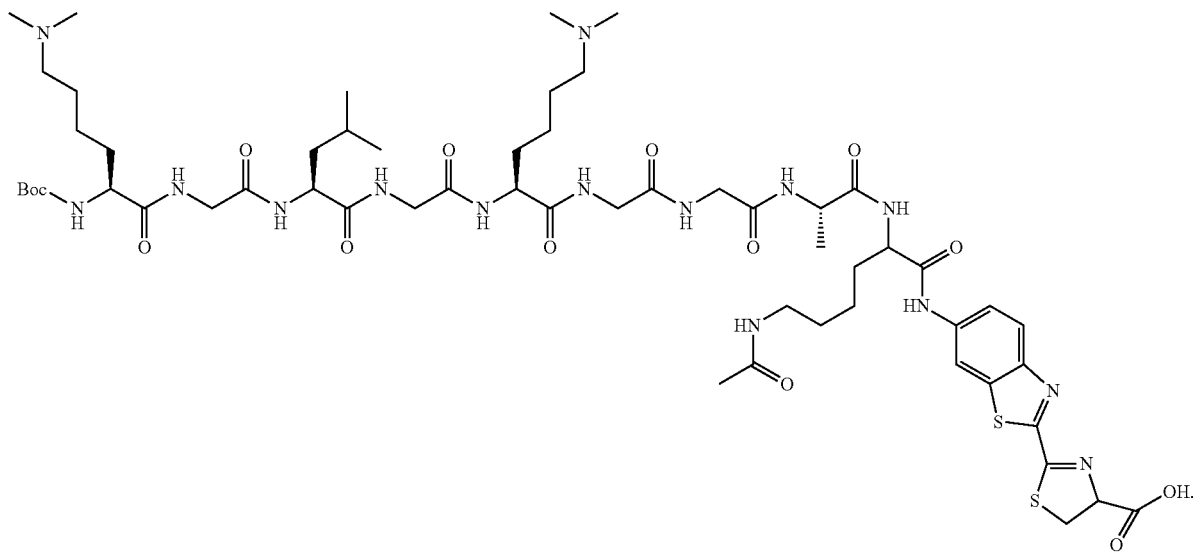

Once the compound of formula (I) has reacted with a HDAC enzyme, the product may be a compound of formula (II):

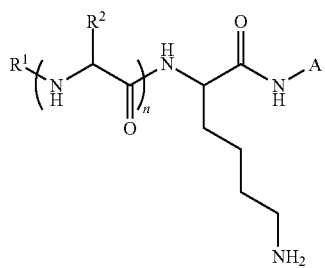

wherein:

A is a reporter moiety;

$R^1$ is selected from H, an amino protecting group and an amino blocking group;

n is an integer from 1 to 20;

each $R^2$ is independently an amino acid side chain, wherein at least one $R^2$ is selected from —$CH_2$—$CH_2$—$CH_2$—$CH_2$—$NR^{4a}R^{4b}$, —$CH_2$—$CH_2$—$CH_2$—$CH_2$—$N^+R^{4a}R^{4b}R^{4c}$ and —$CH_2$—$CH_2$—$CH_2$—NH—C(=$NR^{5a}$)$NR^{5b}R^{5c}$;

each $R^{4a}$ is independently selected from hydrogen, alkyl and aryl;

each $R^{4b}$ is independently selected from alkyl and aryl;

each $R^{4c}$ is independently selected from hydrogen, alkyl and aryl;

each $R^{5a}$ is independently selected from hydrogen, alkyl and aryl;

each $R^{5b}$ is independently selected from alkyl and aryl; and each $R^{5c}$ is independently selected from hydrogen, alkyl and aryl, wherein when $R^2$ is —$CH_2$—$CH_2$—$CH_2$—$CH_2$—$N^+R^{4a}R^{4b}R^{4c}$, the compound further comprises a counteranion.

In some embodiments, the compounds feature an unsubstituted C-terminal lysine residue attached to the reporter. Such compounds may be used to detect the activity of a HAT enzyme, for example. The C-terminal lysine residue is acetylated by a HAT enzyme. An endopeptidase will not recognize or cleave the acetylated compound, but will cleave the unreacted compound to release a reporter moiety, which may then be detected. The activity of the HAT enzyme may be calculated after comparison of the amounts of unreacted compound and reacted compound.

Exemplary peptide substrates of the invention therefore include compounds of formula (II):

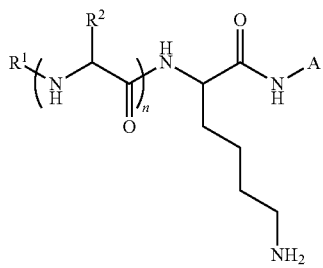

wherein:

A is a reporter moiety;

$R^1$ is selected from H, an amino protecting group and an amino blocking group;

n is an integer from 1 to 20;

each $R^2$ is independently an amino acid side chain, wherein at least one $R^2$ is selected from —$CH_2$—$CH_2$—$CH_2$—$CH_2$—$NR^{4a}R^{4b}$, —$CH_2$—$CH_2$—$CH_2$—$CH_2$—$N^+R^{4a}R^{4b}R^{4c}$ and —$CH_2$—$CH_2$—$CH_2$—NH—C(=$NR^{5a}$)$NR^{5b}R^{5c}$;

each $R^{4a}$ is independently selected from hydrogen, alkyl and aryl;

each $R^{4b}$ is independently selected from alkyl and aryl;

each $R^{4c}$ is independently selected from hydrogen, alkyl and aryl;

each $R^{5a}$ is independently selected from hydrogen, alkyl and aryl;

each $R^{5b}$ is independently selected from alkyl and aryl; and each $R^{5c}$ is independently selected from hydrogen, alkyl and aryl, wherein when R² is —CH₂—CH₂—CH₂—CH₂—N⁺R^{4a}R^{4b}R^{4c}, the compound further comprises a counteranion.

In some embodiments, A is selected from an aminoluciferin, a coumarin, a rhodamine, a coelenterazine, resorufin and cresyl violet.

In some embodiments, R¹ is an amino protecting group or an amino blocking group selected from the group consisting of 9-fluorenylmethyloxycarbonyl (Fmoc), carbobenzyloxy (Cbz), tertbutyloxy (Boc), acetyl and succinyl.

In some embodiments, n is 2, 3, 4 or 5.

In some embodiments, at least one R² is —CH₂—CH₂—CH₂—CH₂—NR^{4a}R^{4b}. In some embodiments, R^{4a} is hydrogen and R^{4b} is methyl. In some embodiments, R^{4a} and R^{4b} are each methyl.

In some embodiments, at least one R² is —CH₂—CH₂—CH₂—CH₂—N⁺R^{4a}R^{4b}R^{4c}. In some embodiments, R^{4a}, R^{4b} and R^{4c} are each methyl.

In some embodiments, at least one R² is —CH₂—CH₂—CH₂—NH—C(=NR^{5a})NR^{5b}R^{5c}. In some embodiments, R^{5a} and R^{5b} are hydrogen and R^{5c} is methyl.

Exemplary compounds of the invention include the following:

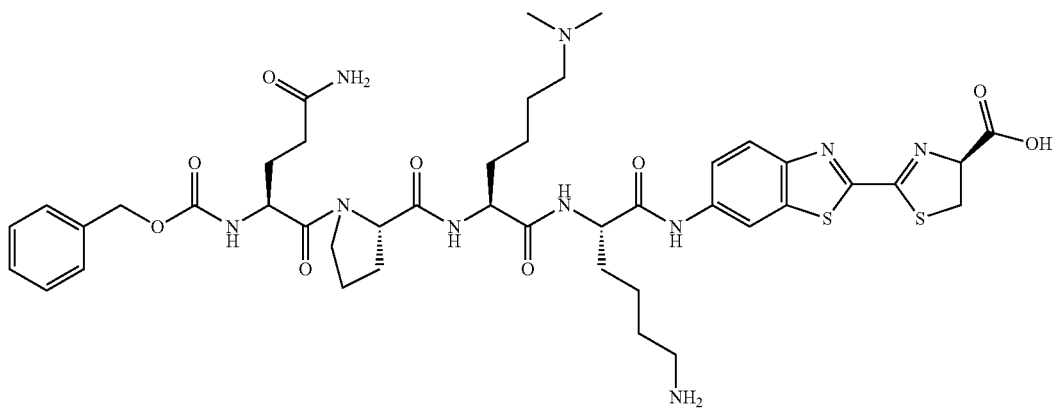

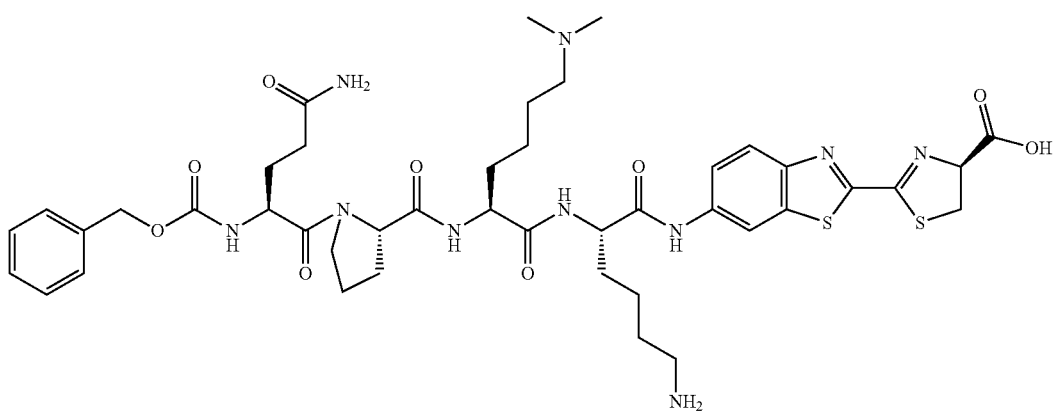

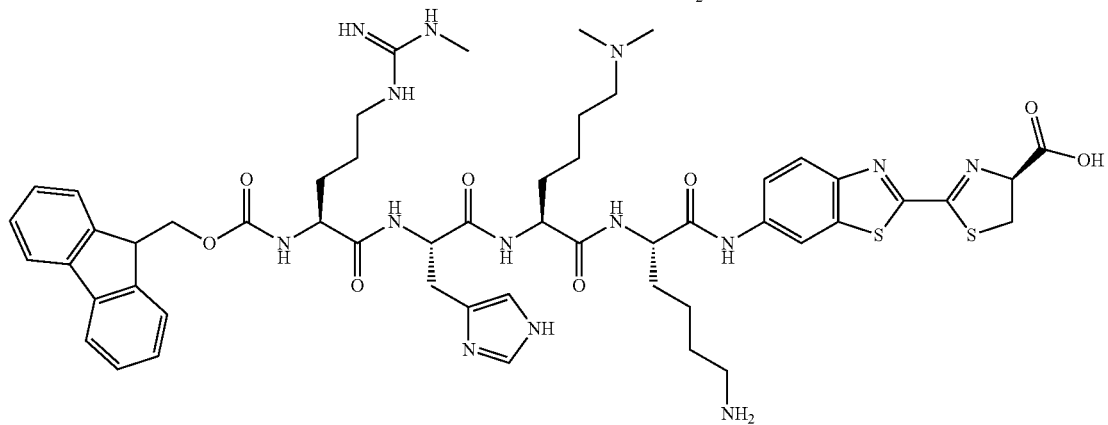

27
28
-continued
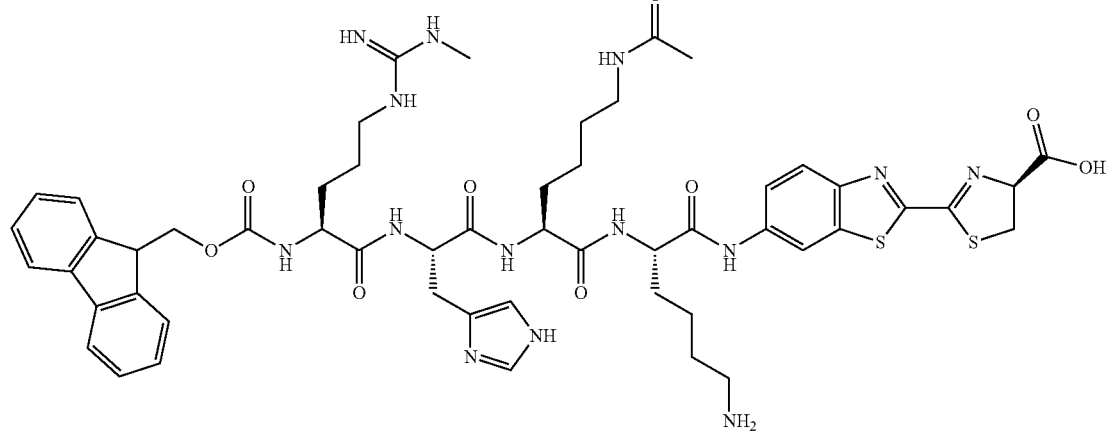
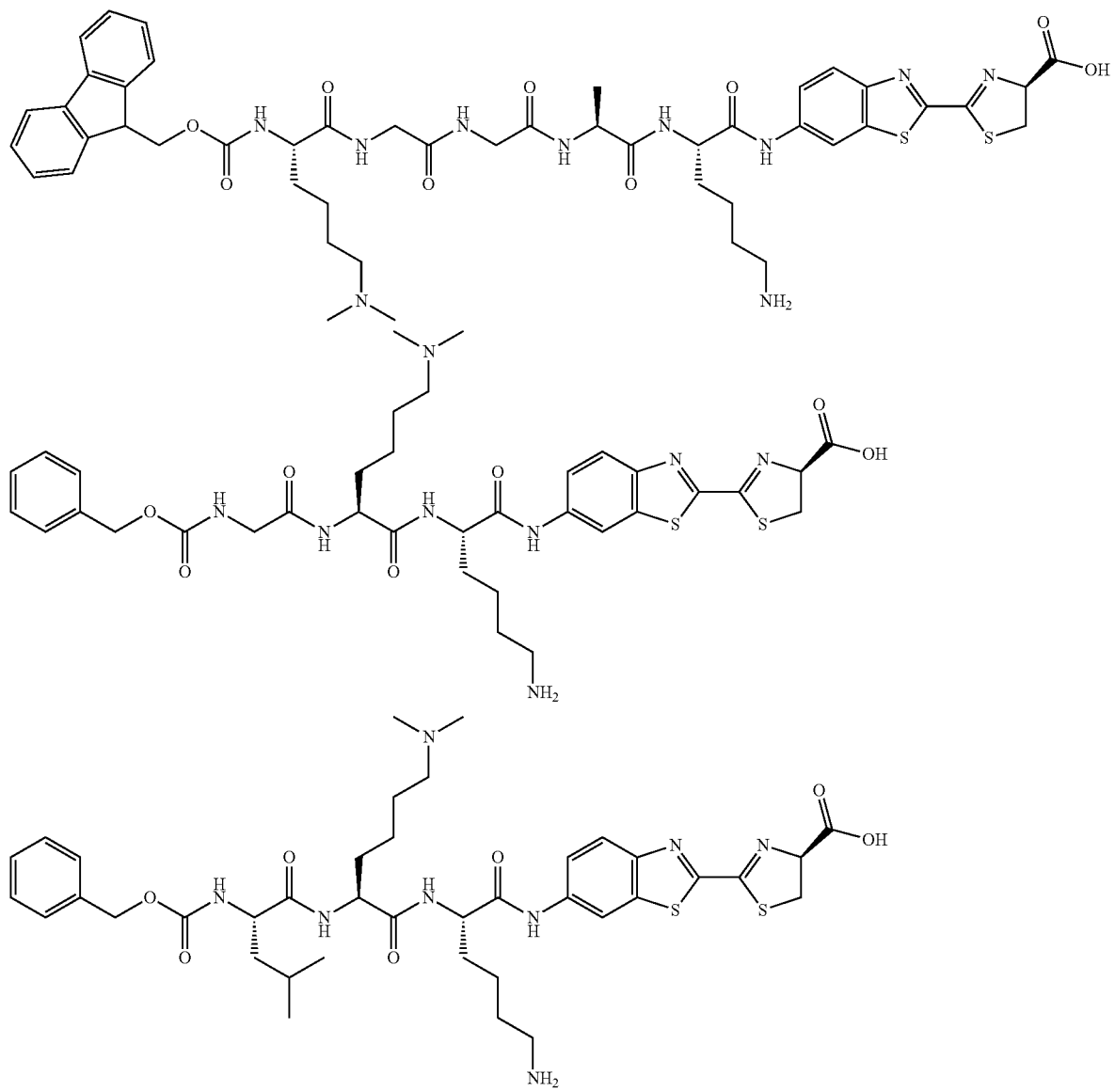

-continued
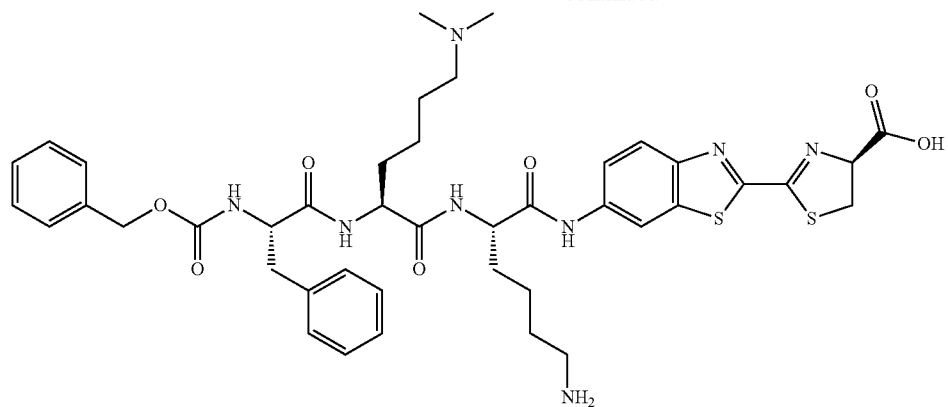
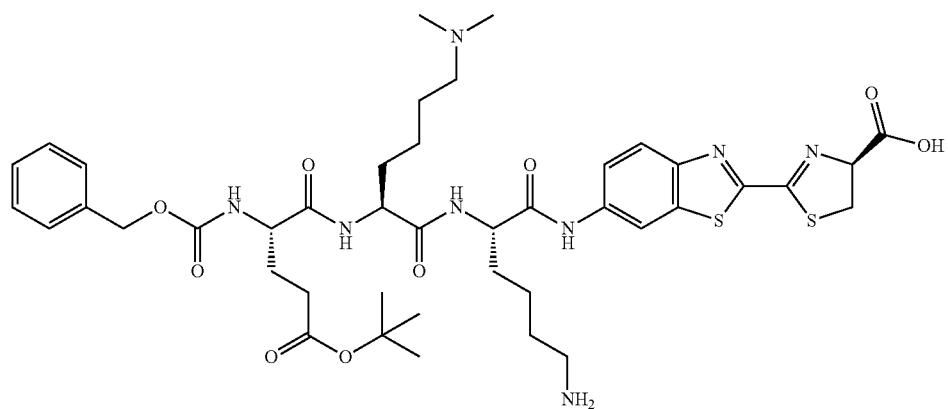
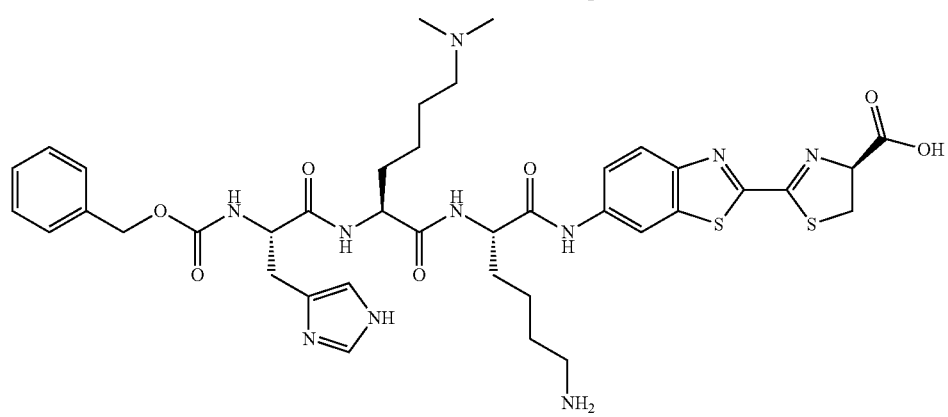
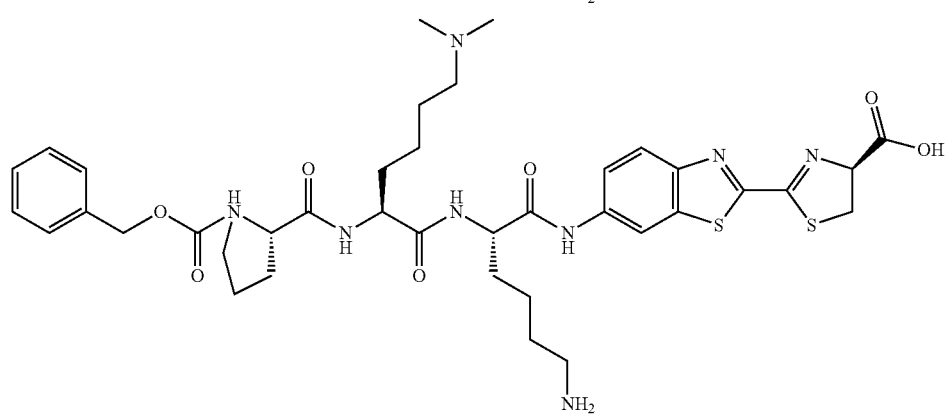

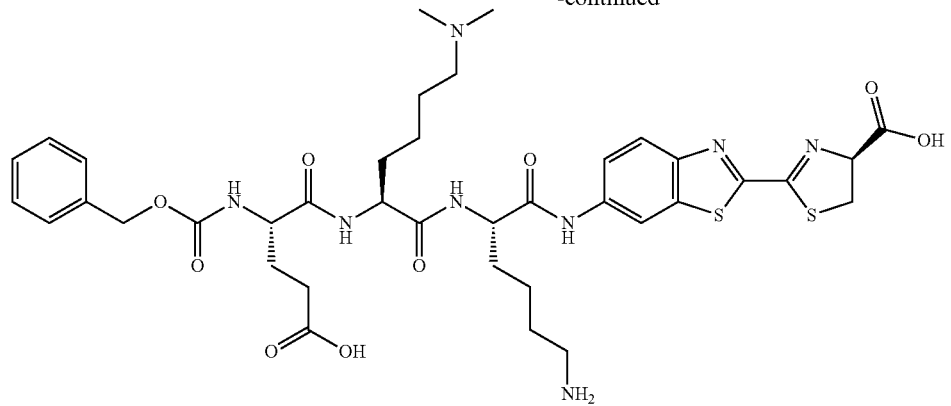
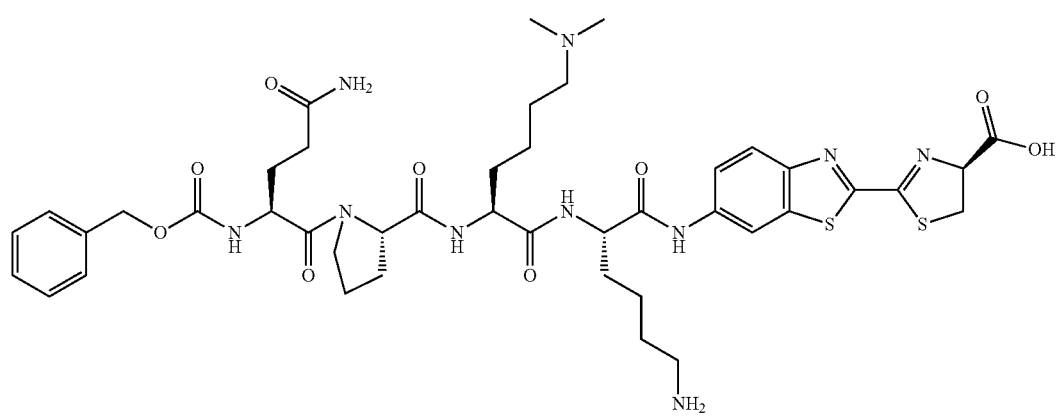
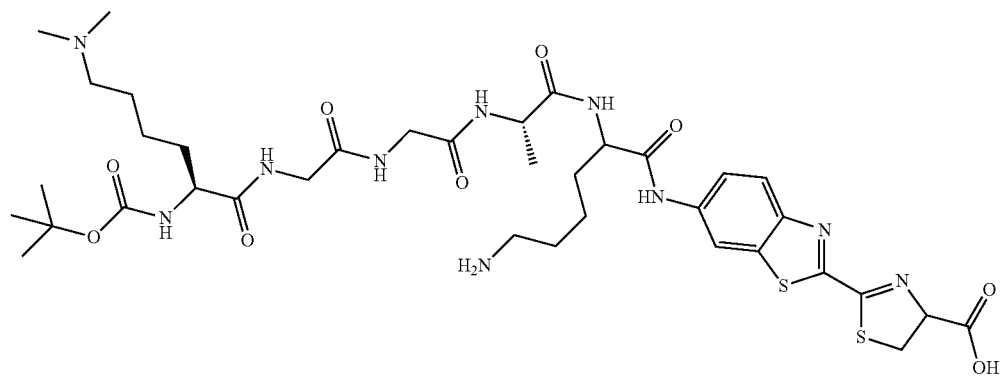

-continued

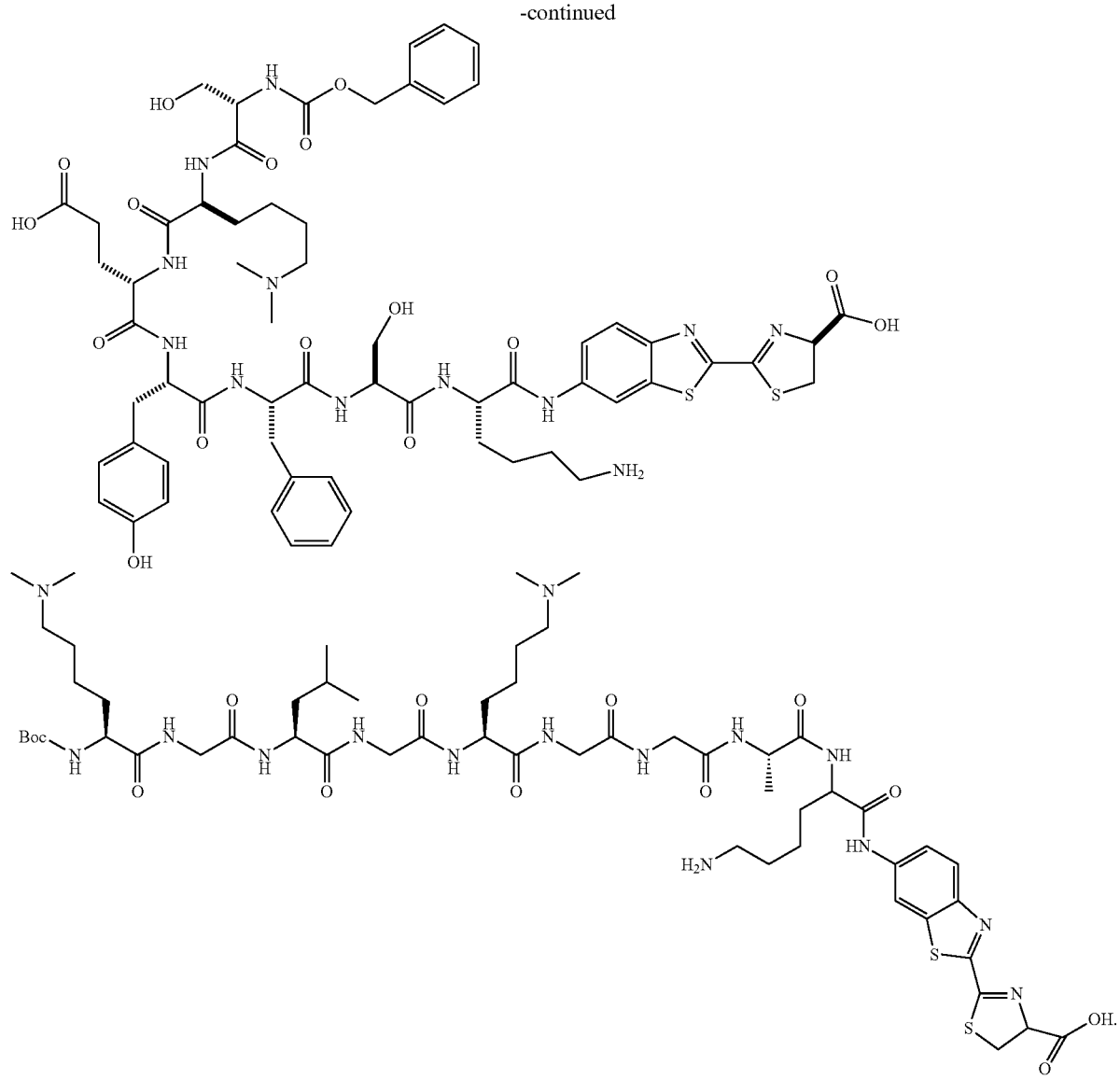

The peptide substrates described herein can be synthesized or manufactured using any technique for peptide synthesis known in the art. For example, the peptides may be prepared using the solid-phase synthetic technique initially described by Merrifield (1963, *J. Am. Chem. Soc.* 85:2149-2154). Other peptide synthesis techniques may be found in Bodanszky et al., *Peptide Synthesis*, John Wiley & Sons, 2d Ed., (1976), *Stuart and Young, Solid Phase Peptide. Synthesis*, Pierce Chemical Company, Rockford, 111, (1984), and other references readily available to those skilled in the art. Peptides may also be synthesized by solution methods as described in *The Proteins, Vol. II,* 3d Ed., Neurath et. al., Eds., p. 105-237, Academic Press, New York, N.Y. (1976). Appropriate protective groups for use in different peptide syntheses are described in the above-mentioned texts as well as in Greene and Wuts, *Protecting Groups In Organic Synthesis,* 3rd edition, John Wiley & Sons, Inc., New York (1999).

The peptide substrates are conjugated to reporter moieties at the carboxy terminus The conjugation may be effected, for example, by conjugating the free carboxy terminus with an amine-containing reporter group using a coupling reagent. Such reagents include, for example: carbodiimides such as dicyclohexylcarbodiimide (DCC) and diisopropylcarbodiimide (DIC); triazoles such as 1-hydroxy-benzotriazole (HOBt) and 1-hydroxy-7-aza-benzotriazole (HOAt); and uronium and phosphonium salts such as HBTU, HATU, HCTU, TBTU and PyBOP. In some embodiments, the reporter moiety or a precursor to the reporter moiety may be coupled to an amino acid, which may subsequently be conjugated to the remainder of the peptide substrate.

Reporter Moieties

The compounds and methods described herein use peptide-based substrates that feature reporter moieties, which under appropriate conditions would directly or indirectly generate a detectable signal. Exemplary reporter moieties include, but are not limited to, fluorophores, luminescent molecules, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal, such as fluorescence or luminescence.

In some embodiments, the reporter moiety may be an aminoluciferin which may produce a luminescent signal upon reaction with luciferase. Luciferase will not react with the aminoluciferin-conjugated peptide substrate. The assay will only generate a luminescent signal when the aminoluciferin has been released from the peptide substrate. The luminescent signal generated may be detected using a luminometer.

In other embodiments, the reporter moiety may be a fluorescent molecule, for example, a coumarin, a rhodamine, a coelenterazine, resorufin or cresyl violet. The fluorescence of the reporter moiety may be quenched when it is conjugated to the peptide substrate, and in such instances, the assay will only generate a signal when the fluorescent molecule has been released from the peptide substrate. Alternatively, the fluorescent reporter moiety may have a different emission wavelength when it is conjugated to the peptide substrate, and the change in emission upon its release from the peptide substrate may be detected. Fluorescence may be detected using a fluorometer.

In other embodiments, the reporter moiety may be a dye whose absorption characteristic changes upon its release from the peptide substrate. Such changes may be detected using a spectrophotometer.

In some embodiments, such as when the reporter moiety is a rhodamine or cresyl violet, the reporter moiety may be further functionalized. For example, when the reporter moiety is a rhodamine or cresyl violet that has two amino groups, one amino group may be the site of attachment to the peptide chain, while the other amino group may be functionalized with a blocking group (e.g., an acyl group such as acetyl). Alternatively, both amino groups may be attached to peptide chains.

Endopeptidases

The endopeptidases used in the methods described herein include those which recognize basic amino acids. They include, for example, trypsin, which is a serine protease that cleaves substrates at the carboxyl side of lysine and arginine residues. Another exemplary endopeptidase is Lys-C, which is a serine protease that cleaves at the carboxyl side of lysine residues. These enzymes do not cleave at the carboxyl side of modified lysine and arginine residues, for example, when the lysine or arginine residue is modified with a protecting group or a blocking group.

Compositions

In some embodiments, the present invention also provides compositions comprising a compound described herein, such as a compound of formula (I) or formula (II), an endopeptidase that recognizes basic amino acids such as trypsin or Lys-C, and optionally a detection reagent. The compositions may also include a buffer, an enzyme cofactor such as NAD$^+$, and/or a target enzyme such as a HDAC or HAT. In a preferred embodiment, the composition comprises a compound of formula (I) or formula (II), an endopeptidase that recognizes basic amino acids such as trypsin or Lys-C, and a luciferin detection reagent.

Kits

In some embodiments, the present invention also provides a kit for use in a method for assaying enzyme activity such as those described herein. A kit may include a compound described herein, such as a compound of formula (I) or formula (II), an endopeptidase that recognizes basic amino acids such as trypsin or Lys-C, and optionally a detection reagent. The kit may further include a buffer, an enzyme cofactor such as NAD$^+$, a control substrate such as a source of HDAC or HAT enzymes (e.g., a nuclear extract from HeLa cells, which includes HDACs), an enzyme inhibitor (e.g., nicotinamide), or an enzyme activator. The kit may also include instructions for carrying out the methods described herein. In a preferred embodiment, the kit comprises a compound of formula (I) or formula (II), an endopeptidase that recognizes basic amino acids such as trypsin or Lys-C, and a luciferin detection reagent.

EXAMPLES

Example 1

Synthesis of H-Lys(Ac)-aminocyanobenzothiazole, trifluoroacetate salt

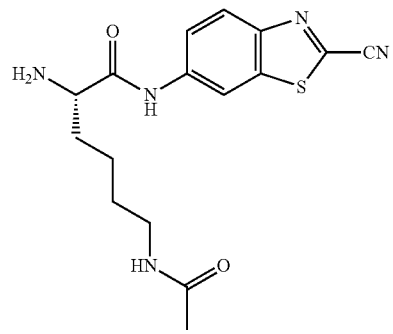 [SMILES: CC(=O)NCCCC[C@H](N)C(=O)Nc1ccc2nc(C#N)sc2c1]

To a stirred solution of Boc-Lys-(Ac)—OH (20.5 g, 71 mmol) in dry THF (410 mL), N-methylmorpholine (7.8 mL, 71 mmol) was added under an atmosphere of $N_2$. The reaction vessel was cooled to 4° C. for 20 minutes, at which time isobutylchloroformate (9.3 mL, 71 mmol) was added dropwise. The reaction was allowed to stir in an ice bath for approximately 60 minutes, at which time 6-amino-2-cyanobenzothiazole (10 g, 57 mM) was added. The reaction was allowed to stir for approximately 30 minutes in the ice bath, removed, and the reaction mixture allowed to reach room temperature overnight. The reaction was then filtered through a Buchner funnel, and the filtrate concentrated to a solid foam. This solid foam was dissolved in dichloromethane (1 L) and washed 2× with NaHCO$_3$ (sat. aq., 300 mL). The organic phase was dried over Na$_2$SO$_4$, filtered, and concentrated to provide a solid foam. This solid foam was then purified by silica gel chromatography with a gradient of heptane/ethyl acetate (EtOAc) (40% EtOAc to 100% EtOAc step gradient over 80 minutes) to provide 24.7 g of Boc-Lys(Ac)-aminocyanobenzothiazole as a foamy solid.

To the foamy solid, a precooled (−20° C.) mixture of thioanisole (48 mL) and trifluoroacetic acid (270 mL) was added under an atmosphere of N$_2$. The progress was monitored by reverse phase HPLC. Once the starting material was consumed, the reaction was concentrated to a thick syrup under high vacuum. This was then purified by silica gel chromatography with a gradient of dichloromethane (DCM)/methanol (MeOH) (5% MeOH to 30% MeOH step gradient over 45 minutes.) to give 22.4 g (85%) of the title compound: $^1$H NMR (DMSO-d$_6$) δ 10.97 (s, 1H), 8.71 (s, 1H), 8.29 (s, 3H), 8.24 (d, 1H), 7.79-7.76 (m, 1H), 3.98 (s, 1H), 2.99 (q, 2H), 1.82 (q, 2H), 1.72 (s, 3H), 1.40-1.33 (m, 4H); MS expected 346 ($C_{16}H_{19}N_5O_2S$, M+1), found 346.

Example 2

Synthesis of H-Lys(TFA)-aminocyanobenzothiazole, trifluoroacetate salt

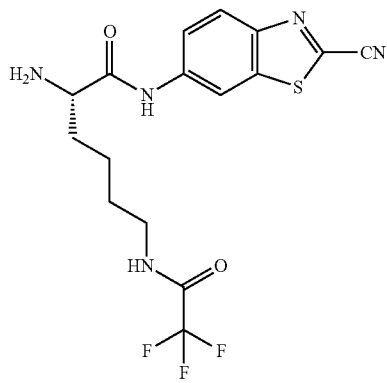 [SMILES: N#Cc1nc2ccc(NC(=O)[C@@H](N)CCCCNC(=O)C(F)(F)F)cc2s1]

This material was synthesized from Boc-Lys(TFA)-OH following the procedure used to synthesize H-Lys(Ac)-aminocyanobenzothiazole (Example 1): $^1$H NMR (DMSO-$d_6$) δ 11.00 (s, 1H), 9.39 (t, 1H), 8.70 (d, 1H), 8.32 (s, 3H), 8.24 (d, 1H), 7.78 (dd, 1H), 4.00 (t, 1H), 3.16 (q, 2H), 1.84 (q, 2H), 1.55-1.46 (m, 2H), 1.41-1.33 (m, 2H); $^{19}$F NMR (DMSO-$d_6$) δ −73.6, −74.4.

Example 3

Synthesis of Cbz-GlnProLys(Me$_2$)Lys(Ac)-aminoluciferin (SEQ ID NO:1)

Step 1. Synthesis of Cbz-Gln(Trt)ProLys(Me$_2$)-OH

2-Cl-Trt resin (12.5 g) was placed into a 500 mL reaction vessel of an Aapptec model #90 peptide synthesizer. The resin was swelled with N-methylpyrrolidinone (NMP). In a separate container, Fmoc-Lys-(Me$_2$)-OH HCl, (5 g, 11.5 mmol) was dissolved in dimethylformamide (DMF; 100 mL). This solution was added to the resin followed by the addition of diisopropylethylamine (DIPEA) (8 mL) and stirred mechanically for 4 hours. At this point, the resin was sequentially washed with DMF and NMP, and then capped 3× with MeOH, with DCM rinses in between each capping step. The resin was then dried under full vacuum overnight to provide Fmoc-Lys-(Me$_2$) 2-Cl Trt resin.

The Fmoc-Lys-(Me$_2$) 2—Cl Trt resin was placed onto the synthesizer, and the Fmoc removed using two washes of 25% piperidine in DMF (10:1 base to resin). A solution of Fmoc-Pro-OH (5.9 g, 17.5 mmol), 1-hydroxybenzothiazole (HOBt, 3.1 g, 23 mmol), O-benzotriazole-N,N,N',N',-tetramethyluronium-hexafluoro-phosphate (HBTU, 7.6 g, 19.9 mmol) and DIPEA (6.9 mL, 39.6 mmol) in NMP (100 mL) was then added to this resin and allowed to mix mechanically for 120 minutes. A Kaiser test was negative for primary amines The reagent solution was then separated from the resin. With a repeat of this protocol, the Fmoc was removed, and Cbz-Gln (Trt)-OH coupled to the resin.

The resin was then washed with MeOH followed by DCM, and this sequence was repeated three times, followed by a final MeOH wash. The resin was then treated with a solution of DCM/acetic acid/trifluoroethanol (100 mL, 8/1/1) and stirred magnetically for 3 hours. The resin was filtered off and rinsed with DCM, and the resulting solution concentrated to provide an oil. Heptane was added, and the solution was concentrated three times. This provided Cbz-Glu(Trt)ProLys (Me$_2$)-OH as a foamy solid (11.97 g, 87%), which was used without further purification.

Step 2. Synthesis of Cbz-Gln(Trt)ProLys(Me$_2$)Lys (Ac)-aminocyanobenzothiazole (SEQ ID NO:3)

To a stirred solution of Cbz-Gln(Trt)ProLys(Me$_2$)-OH (7.4 g, 9.5 mmol) in dry THF (100 mL) under a N$_2$ atmosphere, H-Lys(Ac)-aminocyanobenzothiazole (4.37 g, 9.5 mmol), 1-hydroxyazabenzotriazole (HOAt, 1.3 g, 9.5 mmol) and DIPEA (1.6 mL, 9.5 mmol) was added. Lastly, N-(3-dimethylaminopropyl)-N'-ethylcarbodiimide (EDAC, 1.8 g, 9.5 mmol) was added, and the reaction mixture was allowed to stir at room temperature for 30 minutes. Once the reaction was determined to be complete by reverse phase HPLC (Agilent 1100 HPLC; column: Phenomonex Synergi, 4 µm 80 Å, 250×4.6 mm; method: 30% ACN to 55% ACN over 15 minutes, 1 mL/min, aqueous buffer contains 0.1% TFA v/v), it

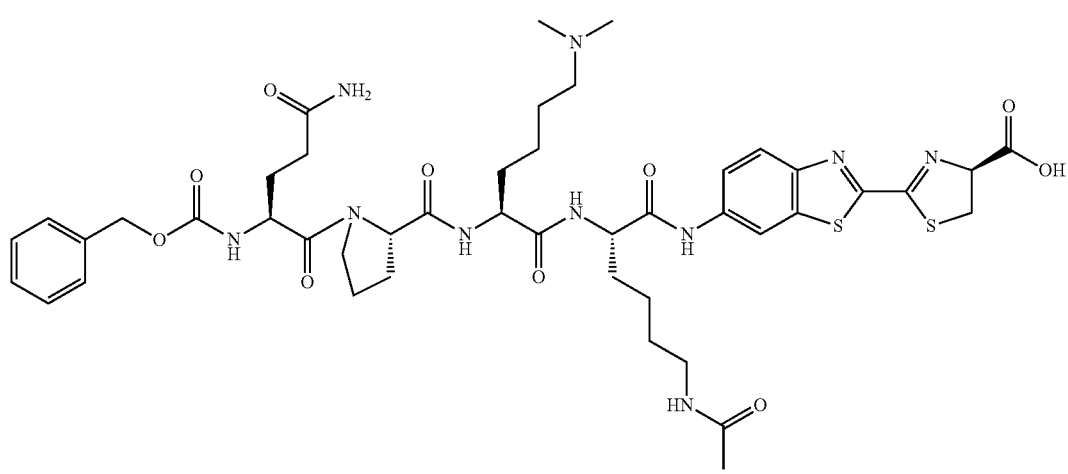

(1)

was concentrated. The resulting solid foam was dissolved in DCM (250 mL) and washed with NaHCO$_3$ (sat. aq., 250 mL). The organic layer was dried over Na$_2$SO$_4$ and concentrated. This material was purified by silica gel chromatography using DCM/MeOH (0% MeOH to 15% MeOH in a step gradient over 20 minutes) to provide Cbz-Gln(Trt)ProLys(Me$_2$)Lys (Ac)-aminocyanobenzothiazole (SEQ ID NO:3) (5.26 g, 51%) as a foamy solid.

Step 3. Synthesis of Cbz-GlnProLys(Me$_2$)Lys(Ac)-aminocyanobenzothiazole (SEQ ID NO:4)

A solution of Cbz-Gln(Trt)ProLys(Me$_2$)Lys(Ac)-aminocyanobenzothiazole (SEQ ID NO:3) (5.26) and triisopropylsilane (4 mL) in TFA/DCM (40 mL, 1/1) was stirred under a N$_2$ atmosphere at −20° C. for 1 hour. After the conversion of starting material to a new species was confirmed by reverse phase HPLC (Agilent 1100 HPLC; column: Phenomonex Synergi, 4 μm 80 Å, 250×4.6 mm. method: 20% ACN to 55% ACN over 15 minutes, 1 mL/min, aqueous buffer contains 0.1% TFA v/v), the reaction mixture was concentrated. The resulting viscous sludge was then flooded with diethyl ether (200 mL), agitated for 5 minutes, and the solids collected via centrifugation and dried under full vacuum to provide crude Cbz-GlnProLys(Me$_2$)Lys(Ac)-aminocyanobenzothiazole (SEQ ID NO:4) (4.4 g).

Step 4. Synthesis of Cbz-GlnProLys(Me$_2$)Lys(Ac)-aminoluciferin (SEQ ID NO:1)

The crude Cbz-GlnProLys(Me$_2$)Lys(Ac)-aminocyanobenzothiazole (SEQ ID NO:4) was dissolved in THF (100 mL) and H$_2$O (50 mL) that had been de-gassed for approximately 5 minutes with a mild stream of N$_2$. To this solution, a similarly de-gassed solution of D-cysteine (0.90 g, 5.1 mmol) and Na$_2$CO$_3$ (0.54 g, 5.1 mmol) in H$_2$O (20 mL) was added, and the reaction stirred for 30 minutes. After the conversion of starting material to a new species was confirmed by reverse phase HPLC (Agilent 1100 HPLC; column: Phenomonex Synergi, 4 μm 80 Å, 250×4.6 mm method: 20% ACN to 55% ACN over 15 minutes, 1 mL/min, aqueous buffer contains 0.1% TFA v/v), the reaction was concentrated to a solid. The crude solid was purified using reverse phase silica gel by preparative HPLC using a gradient of acetonitrile (ACN) in 20 mM NH$_4$OAc (15% ACN to 50% ACN over 60 minutes) to provide the title compound as a white solid (2.75 g, 56%): $^1$H NMR (CD$_3$OD) δ 8.46 (dd, 1H), 7.95 (dd, 1H), 7.63-7.59 (m, 1H), 7.35-7.29 (m, 5H), 5.21 (dt, 2H), 5.06 (s, 2H), 4.47-4.38 (m, 3H), 3.73 (d, 3H), 3.14-3.01 (m, 4H), 2.79 (s, 3H), 2.75 (t, 2H), 2.35 (t, 2H), 2.23-1.71 (m, 18H), 1.54-1.46 (m, 4H); MS expected 966 (C$_{45}$H$_{60}$N$_{10}$O$_{10}$S$_2$, M+1), found 966.

Example 4

Synthesis of Additional Compounds

Cbz-GlnProLys(Me$_2$)Lys(TFA)-aminoluciferin (SEQ ID NO:5) (2)

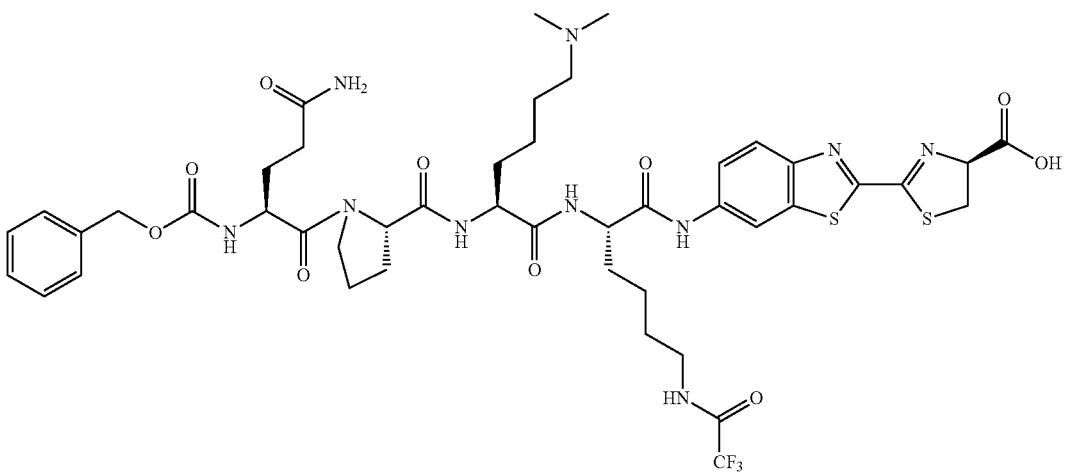

(2)

This compound was synthesized from Cbz-Gln(Trt) ProLys(Me$_2$)-OH and H-Lys(TFA)-aminocyanobenzothiazole following the procedure used to synthesize Cbz-Gln-ProLys(Me$_2$)Lys(Ac)-aminoluciferin (SEQ ID NO:1) (Example 3): $^1$H NMR (DMSO-d$_6$) δ 10.64 (d, 1H), 9.47 (s, 1H), 8.64 (s, 1H), 8.49 (d, 1H), 8.07-7.98 (m, 2H), 7.77 (dd, 1H), 7.51 (d, 1H), 7.34-7.29 (m, 5H), 6.78 (s, 1H), 5.18 (t, 1H), 4.98 (s, 2H), 4.34-4.22 (m, 4H), 3.75 (q, 1H), 3.67-3.58 (m, 3H), 3.15 (q, 2H), 2.43-2.38 (m, 2H), 2.28 (d, 6H), 2.21 (t, 2H), 2.12 (t, 2H), 2.05-1.94 (m, 2H), 1.87-1.63 (m, 8H), 1.51-1.28 (m, 10H).

Fmoc-Arg(Me)HisLys(Ac)Lys(Ac)-aminoluciferin (SEQ ID NO:6) (3)

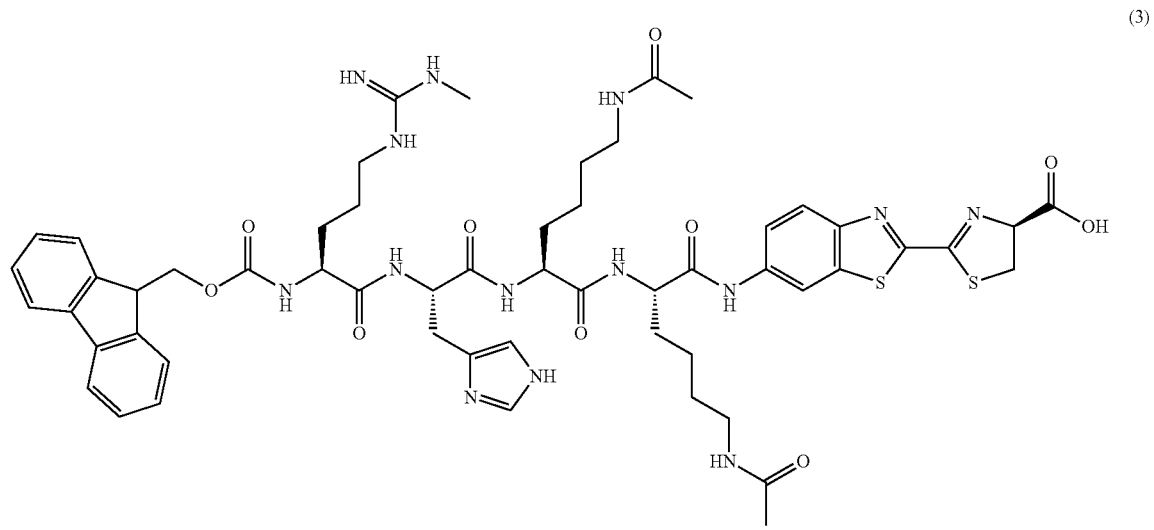 [SMILES: CNC(=N)NCCC[C@H](NC(=O)OCC1c2ccccc2-c2ccccc21)C(=O)N[C@@H](Cc1c[nH]cn1)C(=O)N[C@@H](CCCCNC(C)=O)C(=O)N[C@@H](CCCCNC(C)=O)C(=O)Nc1ccc2nc(C3=N[C@@H](C(=O)O)CS3)sc2c1]

(3)

This compound was synthesized from Fmoc-Arg(Me)(Pbf)His(Trt)Lys(Ac)—OH and H-Lys(Ac)-aminocyanobenzothiazole following the procedure used to synthesize Cbz-GlnProLys(Me$_2$)Lys(Ac)-aminoluciferin (SEQ ID NO:1) (Example 3). Fmoc-Arg(Me)(Pbf)His(Trt)Lys(Ac)—OH was synthesized using Fmoc-Arg(Me)(Pbf)-OH, Fmoc-His(Trt)-OH and Fmoc-Lys(Ac)—OH following the procedure used to synthesize Cbz-GlnProLys(Me$_2$)-OH (Example 3) on solid support: $^1$H NMR (DMSO-d$_6$ and D$_2$O) δ 8.40 (d, 1H), 7.99 (t, 1H), 7.84 (d, 4H), 7.66 (d, 2H), 7.40 (d, 2H), 7.36-7.26 (m, 2H), 5.03 (t, 1H), 4.35-4.26 (m, 2H), 4.22-4.19 (m, 2H), 4.03-3.97 (m, 1H), 3.56-3.53 (m, 2H), 3.04-2.87 (m, 8H), 2.68-2.63 (m, 3H), 1.83 (s, 3H), 1.74 (s, 3H), 1.67-1.48 (m, 6H), 1.36-1.14 (m, 6H).

Fmoc-Lys(Me$_2$)GlyGlyAlaLys(Ac)-aminoluciferin
(SEQ ID NO:7) (4)

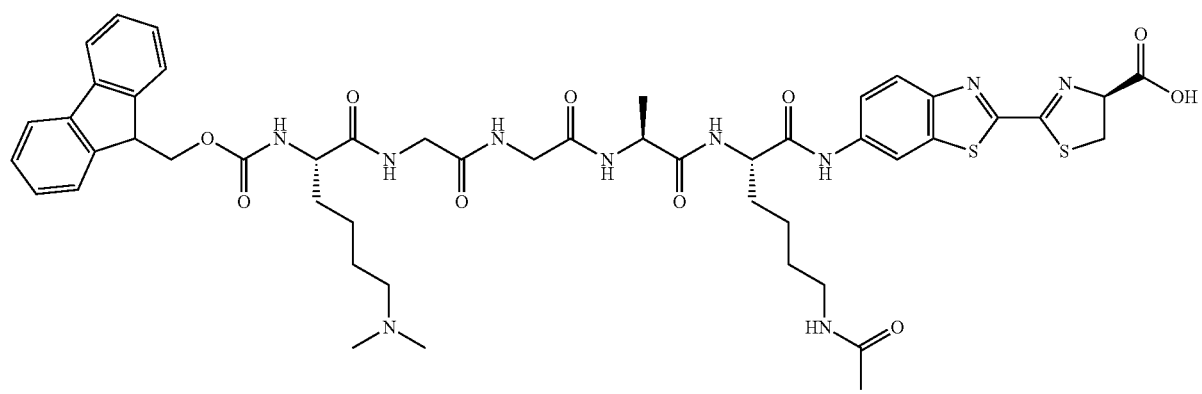

(4)

This compound was synthesized from Fmoc-Lys(Me$_2$)GlyGlyAla-OH (SEQ ID NO:8) and H-Lys(Ac)-aminocyanobenzothiazole following the procedure used to synthesize Cbz-GlnProLys(Me$_2$)Lys(Ac)-aminoluciferin (SEQ ID NO:1) (Example 3). Fmoc-Lys(Me$_2$)GlyGlyAla-OH (SEQ ID NO:8) was synthesized using Fmoc-Lys(Me$_2$)-OH, Fmoc-Gly-OH and Fmoc-Ala-OH following the procedure used to synthesize Cbz-GlnProLys(Me$_2$)-OH (Example 3) on solid support: $^1$H NMR (CD$_3$OD) δ 7.92 (dd, 1H), 7.85 (dd, 1H), 7.79-7.71 (m, 2H), 7.67-7.57 (m, 3H), 7.40-7.20 (m, 4H), 5.20 (td, 1H), 4.45-4.10 (m, 5H), 4.00-3.67 (m, 7H), 3.14 (dt, 2H), 3.07-2.95 (m, 3H), 2.81 (s, 3H), 2.80 (d, 2H), 1.95 (s, 6H), 1.89 (d, 3H), 1.87-1.62 (m, 4H), 1.48-1.34 (m, 6H); MS expected 1014 (C$_{49}$H$_{60}$N$_{10}$O$_{10}$S$_2$, M+1), found 1014.

Cbz-GlyLys(Me$_2$)Lys(Ac)-aminoluciferin (5)

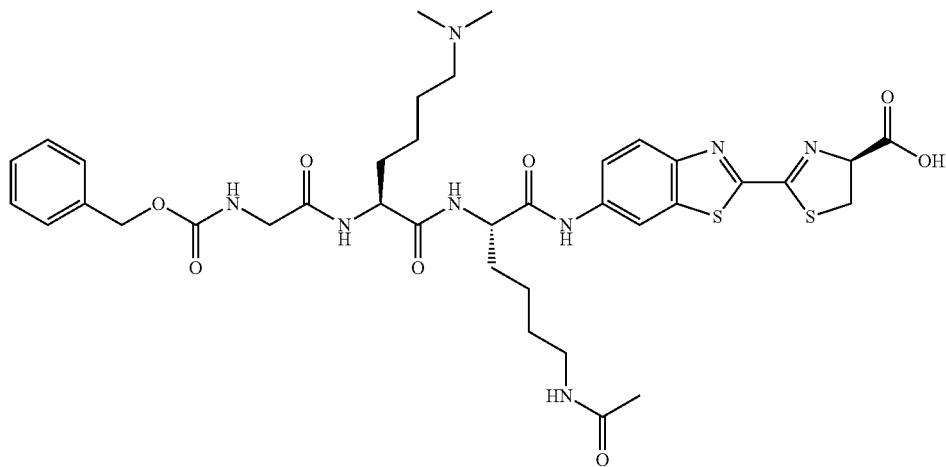

(5)

This compound was synthesized from Cbz-GlyLys(Me$_2$)-OH and H-Lys(Ac)-aminocyanobenzothiazole following steps 1, 2 and 4 of the procedure used to synthesize Cbz-GlnProLys(Me$_2$)Lys(Ac)-aminoluciferin (SEQ ID NO:1) (Example 3). In step 1, Cbz-GlyLys(Me$_2$)-OH was synthesized using Cbz-Gly-OH and Fmoc-Lys(Me$_2$)-OH following the procedure used to synthesize Cbz-GlnProLys(Me$_2$)-OH (Example 3) on solid support: MS expected 798 (C$_{37}$H$_{48}$N$_8$O$_8$S$_2$, M+1), found 798.

Cbz-LeuLys(Me$_2$)Lys(Ac)-aminoluciferin (6)

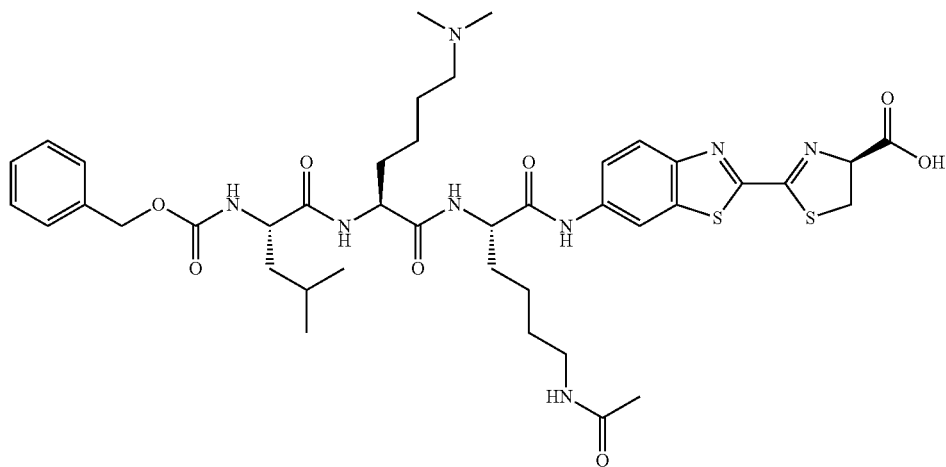

(6)

This compound was synthesized from Cbz-LeuLys(Me₂)-OH and H-Lys(Ac)-aminocyanobenzothiazole following steps 1, 2 and 4 of the procedure used to synthesize Cbz-GlnProLys(Me₂)Lys(Ac)-aminoluciferin (Example 3). In step 1, Cbz-LeuLys(Me₂)-OH was synthesized using Cbz-Leu-OH and Fmoc-Lys(Me₂)-OH following the procedure used to synthesize Cbz-GlnProLys(Me₂)-OH (Example 3) on solid support: MS expected 854 ($C_{41}H_{56}N_8O_8S_2$, M+1), found 854.

Cbz-PheLys(Me₂)Lys(Ac)-aminoluciferin (7)

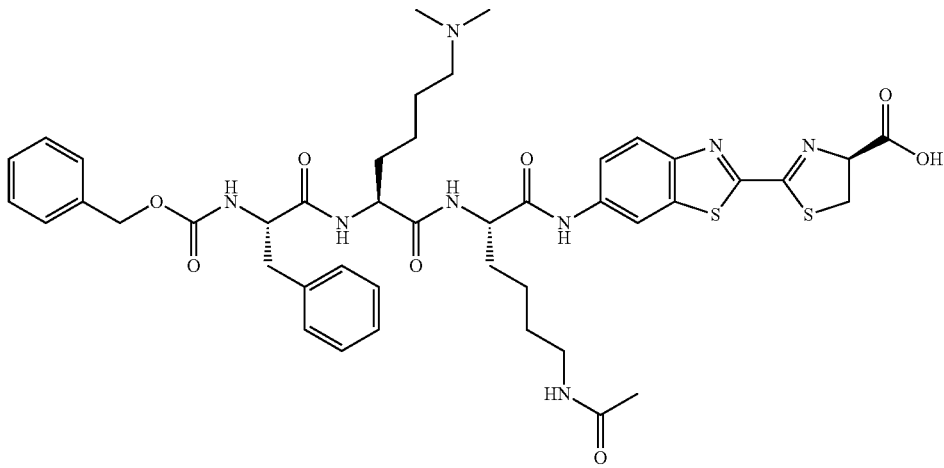

(7)

This compound was synthesized from Cbz-PheLys(Me₂)-OH and H-Lys(Ac)-aminocyanobenzothiazole following steps 1, 2 and 4 of the procedure used to synthesize Cbz-GlnProLys(Me₂)Lys(Ac)-aminoluciferin (Example 3). In step 1, Cbz-PheLys(Me₂)-OH was synthesized using Cbz-Phe-OH and Fmoc-Lys(Me₂)-OH following the procedure used to synthesize Cbz-GlnProLys(Me₂)-OH (Example 3) on solid support: MS expected 888 ($C_{44}H_{54}N_8O_8S_2$, M+1), found 888.

Cbz-Glu(tBu)Lys(Me₂)Lys(Ac)-aminoluciferin (8)

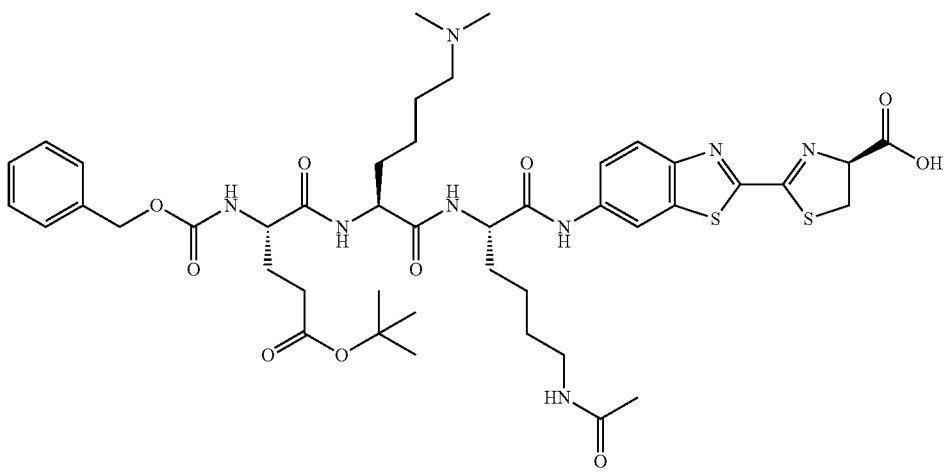

(8)

This compound was synthesized from Cbz-Glu(tBu)Lys(Me₂)-OH and H-Lys(Ac)-aminocyanobenzothiazole following steps 1, 2 and 4 of the procedure used to synthesize Cbz-GlnProLys(Me₂)Lys(Ac)-aminoluciferin (Example 3). In step 1, Cbz-Glu(tBu)Lys(Me₂)-OH was synthesized using Cbz-Glu(tBu)-OH and Fmoc-Lys(Me₂)-OH following the procedure used to synthesize Cbz-GlnProLys(Me₂)-OH (Example 3) on solid support: MS expected 926 ($C_{44}H_{60}N_8O_{10}S_2$, M+1), found 926.

Cbz-HisLys(Me₂)Lys(Ac)-aminoluciferin (9)

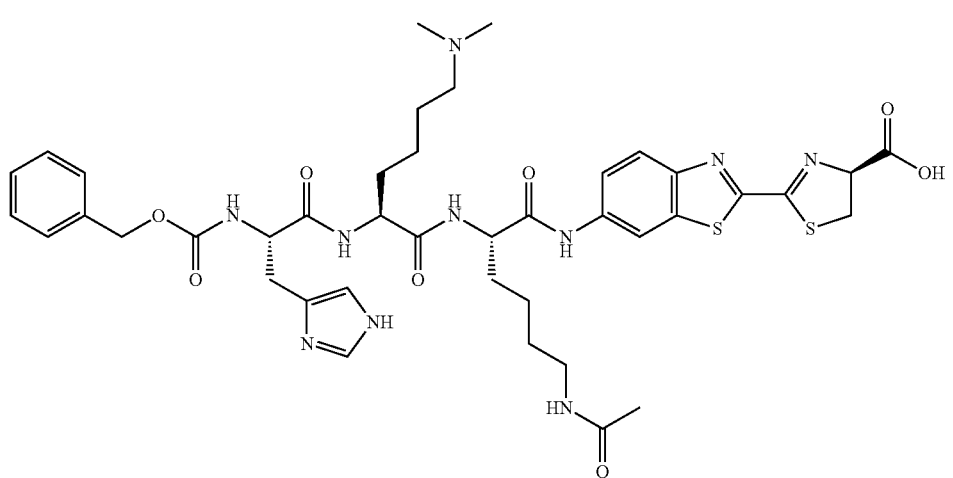

(9)

This compound was synthesized from Cbz-HisLys(Me₂)-OH and H-Lys(Ac)-aminocyanobenzothiazole following steps 1, 2 and 4 of the procedure used to synthesize Cbz-GlnProLys(Me₂)Lys(Ac)-aminoluciferin (Example 3). In step 1, Cbz-HisLys(Me₂)-OH was synthesized using Cbz-His-OH and Fmoc-Lys(Me₂)-OH following the procedure used to synthesize Cbz-GlnProLys(Me₂)-OH (Example 3) on solid support: MS expected 878 ($C_{41}H_{52}N_{10}O_8S_2$, M+1), found 878.

Cbz-ProLys(Me₂)Lys(Ac)-aminoluciferin (10)

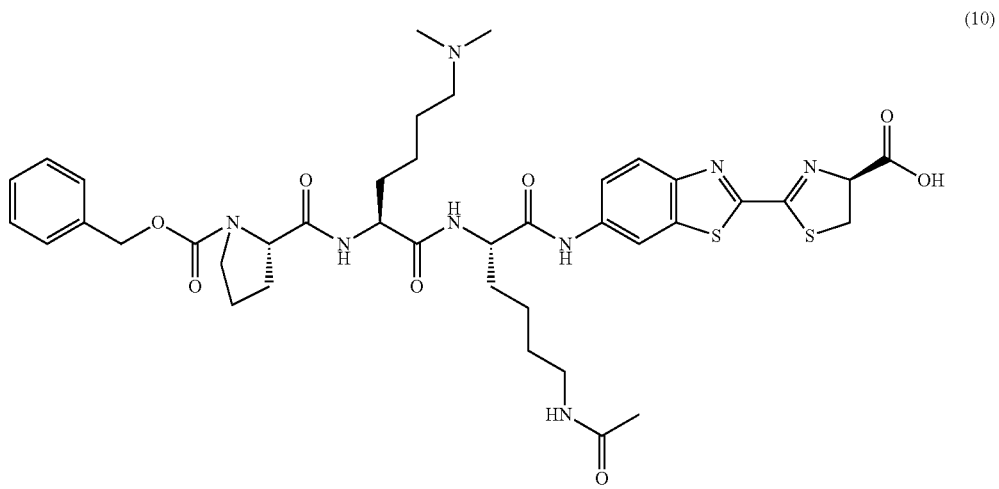 [SMILES: CC(=O)NCCCC[C@H](NC(=O)[C@H](CCCCN(C)C)NC(=O)[C@@H]1CCCN1C(=O)OCc1ccccc1)C(=O)Nc1ccc2nc(C3=N[C@@H](C(=O)O)CS3)sc2c1]

(10)

This compound was synthesized from Cbz-ProLys(Me₂)-OH and H-Lys(Ac)-aminocyanobenzothiazole following steps 1, 2 and 4 of the procedure used to synthesize Cbz-GlnProLys(Me₂)Lys(Ac)-aminoluciferin (Example 3). In step 1, Cbz-ProLys(Me₂)-OH was synthesized using Cbz-Pro-OH and Fmoc-Lys(Me₂)-OH following the procedure used to synthesize Cbz-GlnProLys(Me₂)-OH (Example 3) on solid support: MS expected 838 ($C_{40}H_{52}N_8O_8S_2$, M+1), found 838.

Cbz-GluLys(Me₂)Lys(Ac)-aminoluciferin (11)

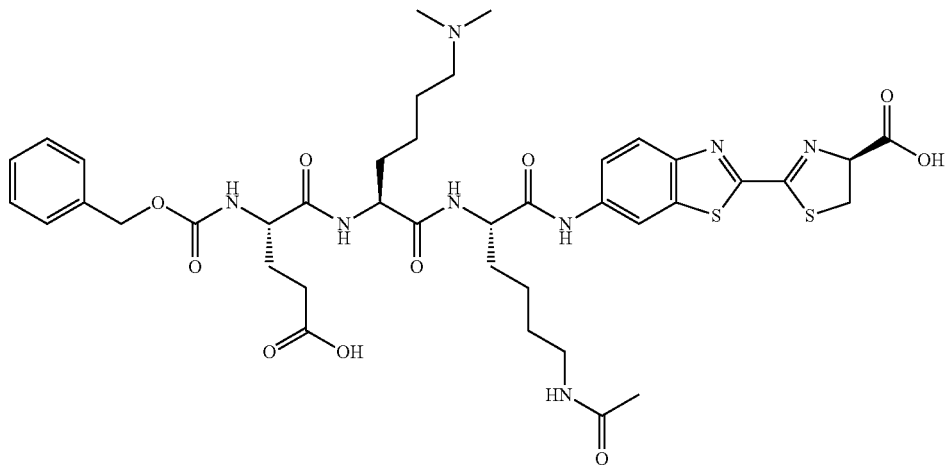

(11)

This compound was synthesized from Cbz-Glu(tBu)Lys(Me₂)Lys(Ac)-aminoluciferin following step 3 of the procedure used to synthesize Cbz-GlnProLys(Me₂)Lys(Ac)-aminoluciferin (SEQ ID NO:1) (Example 3): MS expected 870 ($C_{40}H_{52}N_8O_{10}S_2$, M+1), found 870.

Boc-Lys(Me₂)GlyGlyAlaLys(Ac)-aminoluciferin (SEQ ID NO:9) (12)

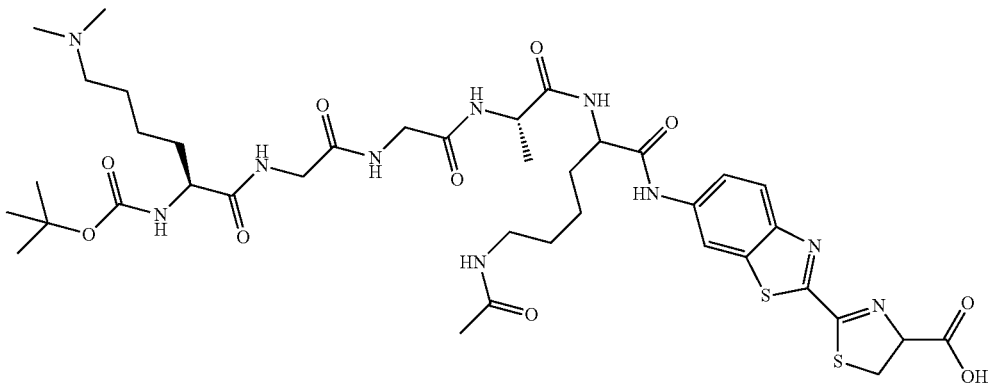

(12)

This compound was synthesized from Boc-Lys(Me$_2$)GlyGlyAla-OH (SEQ ID NO:10) and H-Lys(Ac)-aminocyanobenzothiazole following the procedure used to synthesize Cbz-GlnProLys(Me$_2$)Lys(Ac)-aminoluciferin (SEQ ID NO:1) (Example 3). Boc-Lys(Me$_2$)GlyGlyAla-OH (SEQ ID NO:10) was synthesized using Boc-Lys(Me$_2$)-OH, Fmoc-Gly-OH and Fmoc-Ala-OH following the procedure used to synthesize Cbz-GlnProLys(Me$_2$)-OH (Example 3) on solid support: MS expected 892 (C$_{39}$H$_{59}$N$_{10}$O$_{10}$S$_2$, M+1), found 892.

Boc-Lys(Me$_2$)GlyGlyAlaLys(TFA)-aminoluciferin (SEQ ID NO:11) (13)

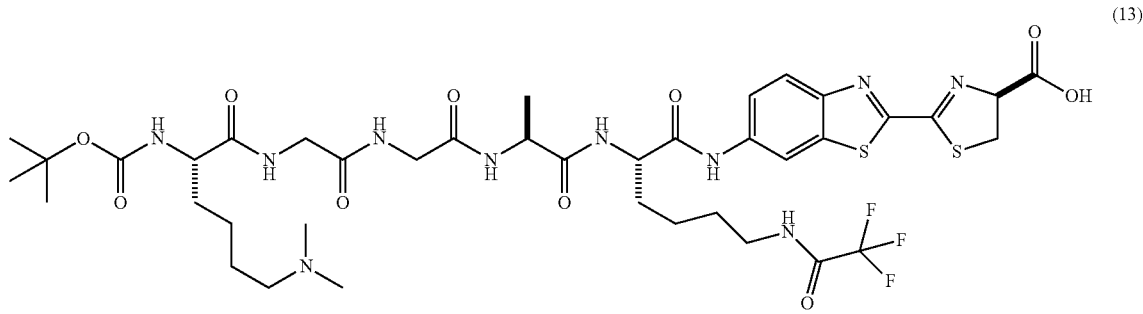 [SMILES: C[C@H](NC(=O)CNC(=O)CNC(=O)[C@H](CCCCN(C)C)NC(=O)OC(C)(C)C)C(=O)N[C@@H](CCCCNC(=O)C(F)(F)F)C(=O)Nc1ccc2nc(C3=N[C@@H](C(=O)O)CS3)sc2c1]

(13)

This compound was synthesized from Boc-Lys(Me$_2$)GlyGlyAla-OH (SEQ ID NO:10) and H-Lys(TFA)-aminocyanobenzothiazole following the procedure used to synthesize Cbz-GlnProLys(Me$_2$)Lys(Ac)-aminoluciferin (SEQ ID NO:1) (Example 3): MS expected 945 (C$_{39}$H$_{56}$F$_3$N$_{10}$O$_{10}$S2, M+1), found 945.

Cbz-SerLys(Me$_2$)GluTyrPheSerLys(Ac)-aminoluciferin (SEQ ID NO:12) (14)

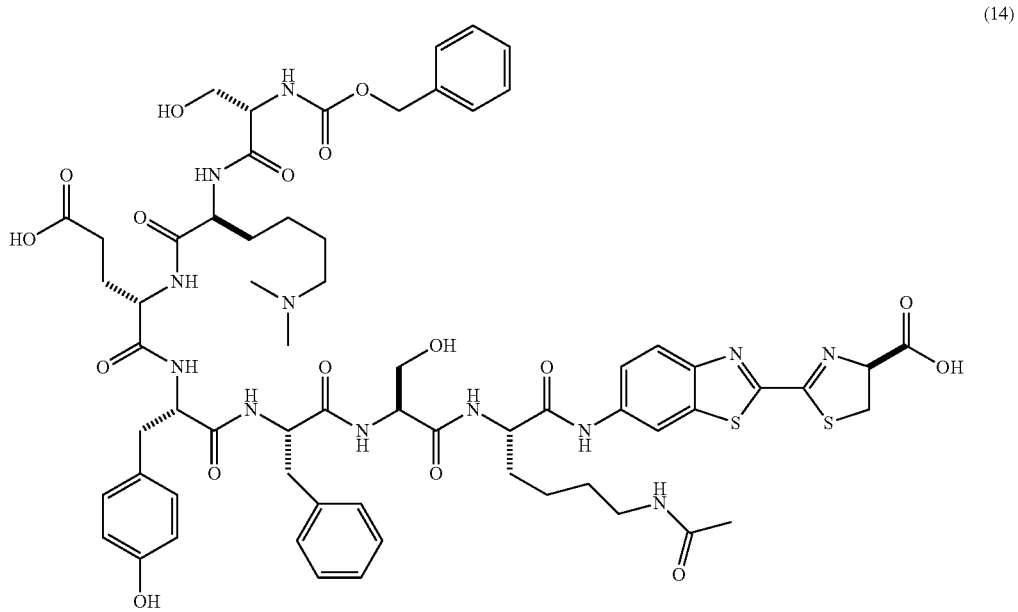

(14)

This compound was synthesized from Cbz-SerLys(Me$_2$)GluTyrPheSer-OH (SEQ ID NO:13) and H-Lys(Ac)-aminocyanobenzothiazole following the procedure used to synthesize Cbz-GlnProLys(Me$_2$)Lys(Ac)-aminoluciferin (SEQ ID NO:1) (Example 3). Cbz-SerLys(Me$_2$)GluTyrPheSer-OH (SEQ ID NO:13) was synthesized following the procedure used to synthesize Cbz-GlnProLys(Me$_2$)-OH (Example 3) on solid support: MS expected 1354 (C$_{64}$H$_{81}$N$_{12}$O$_{17}$S$_2$, M+1), found 1354.

Boc-Lys(Me$_2$)GlyLeuGlyLys(Me$_2$)GlyGlyAlaLys(Ac)-aminoluciferin (SEQ ID NO:14) (15)

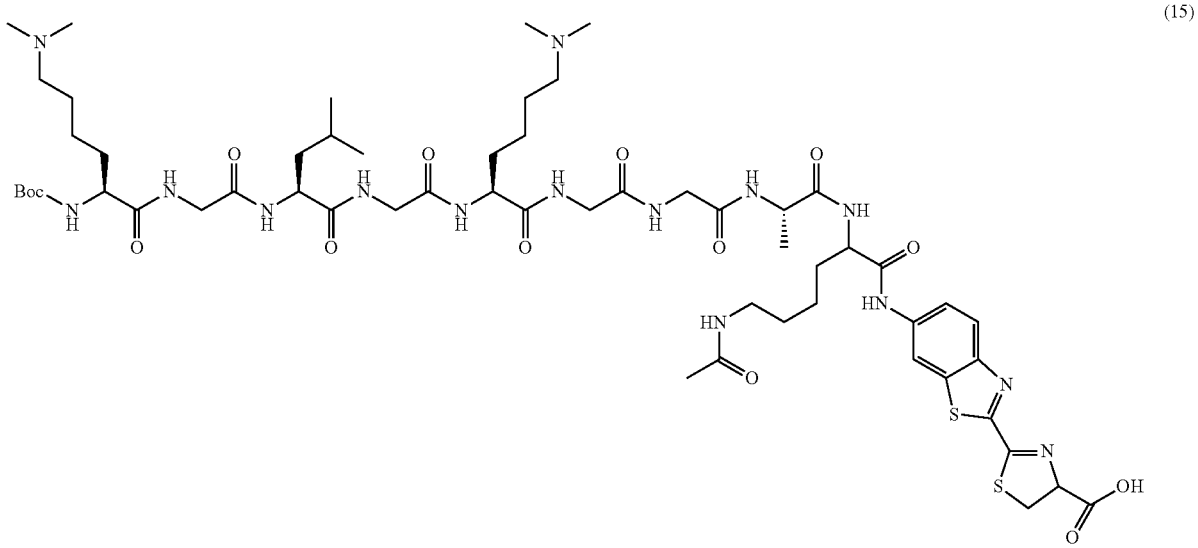 [SMILES: CC(=O)NCCCCC(NC(=O)[C@H](C)NC(=O)CNC(=O)CNC(=O)[C@H](CCCCN(C)C)NC(=O)CNC(=O)[C@H](CC(C)C)NC(=O)CNC(=O)[C@H](CCCCN(C)C)NC(=O)OC(C)(C)C)C(=O)Nc1ccc2nc(C3=NC(C(=O)O)CS3)sc2c1]

(15)

This compound was synthesized from Boc-Lys(Me$_2$)GlyLeuGlyLys(Me$_2$)GlyGlyAla-OH (SEQ ID NO:15) and H-Lys(Ac)-aminocyanobenzothiazole following the procedure used to synthesize Cbz-GlnProLys(Me$_2$)Lys(Ac)-aminoluciferin (SEQ ID NO:1) (Example 3). Boc-Lys(Me$_2$)GlyLeuGlyLys(Me$_2$)GlyGlyAla-OH (SEQ ID NO:15) was synthesized following the procedure used to synthesize Cbz-GlnProLys(Me$_2$)-OH (Example 3) on solid support: MS expected 638 (C$_{57}$H$_{93}$N$_{15}$O$_{14}$S$_2$, (M+2)/2), found 638.

Cbz-GlnProLys(Me$_2$)Lys-aminoluciferin (SEQ ID NO:2) (16)

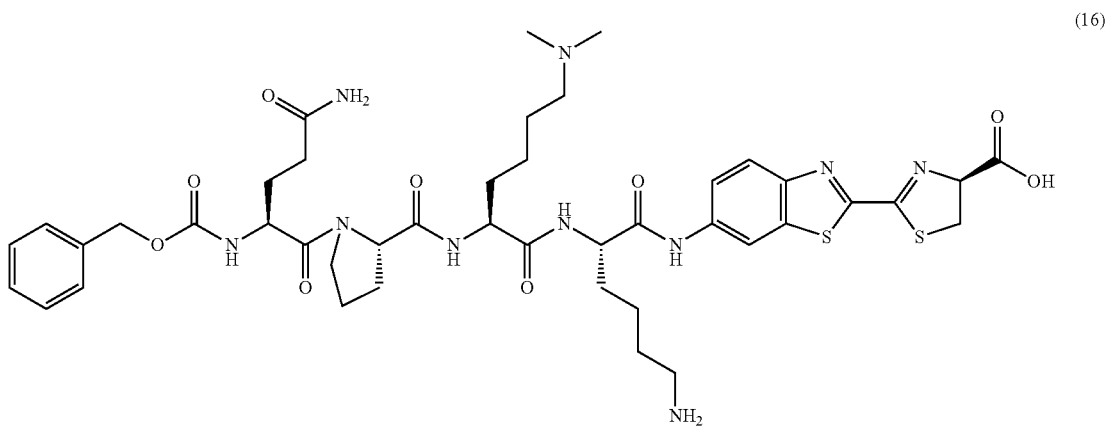 [SMILES: CN(C)CCCC[C@H](NC(=O)[C@@H]1CCCN1C(=O)[C@H](CCC(N)=O)NC(=O)OCc1ccccc1)C(=O)N[C@@H](CCCCN)C(=O)Nc1ccc2nc(C3=N[C@@H](C(=O)O)CS3)sc2c1]

(16)

This compound was synthesized by coupling Cbz-Gln(Trt)ProLys(Me₂)-OH and H-Lys(Boc)-aminocyanobenzothiazole using the procedure used to synthesize Cbz-GlnProLys(Me₂)Lys(Ac)-aminoluciferin (SEQ ID NO:1) (Example 3). H-Lys(Boc)-aminocyanobenzothiazole was synthesized by coupling Fmoc-Lys(Boc)-OH and aminocyanobenzothiazole using the procedure for Boc-Lys(Ac)—OH (Example 1) followed by Fmoc deprotection as described in the synthesis of Cbz-Gln(Trt)ProLys(Me₂)-OH (Example 3): ¹H NMR (DMSO-d₆) δ 11.09 (s, 1H), 9.00 (s, 1H), 8.71 (s, 1H), 8.33 (s, 1H), 8.20 (s, 1H), 8.07-8.01 (m, 1H), 7.89 (t, 2H), 7.58 (d, 1H), 7.38-7.28 (m, 5H), 6.79 (s, 2H), 5.21-5.11 (m, 1H), 4.98 (s, 2H), 4.38-4.20 (m, 3H), 3.85-3.76 (m, 1H), 3.67-3.56 (m, 2H), 2.84-2.70 (m, 1H), 2.17-2.07 (m, 4H), 2.05-1.90 (m, 14H), 1.84 (s, 6H), 1.69-1.50 (m, 7H), 1.43-1.20 (m, 4H).

Boc-Lys(Me₂)GlyGlyAlaLys-aminoluciferin (SEQ ID NO:16) (17)

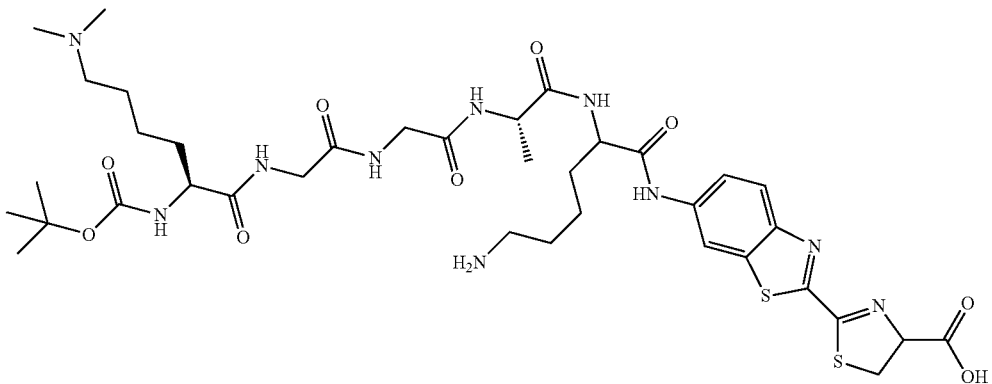

(17)

This compound will be synthesized in a manner similar to compound 12.

Cbz-SerLys(Me₂)GluTyrPheSerLys-aminoluciferin (SEQ ID NO:17) (18)

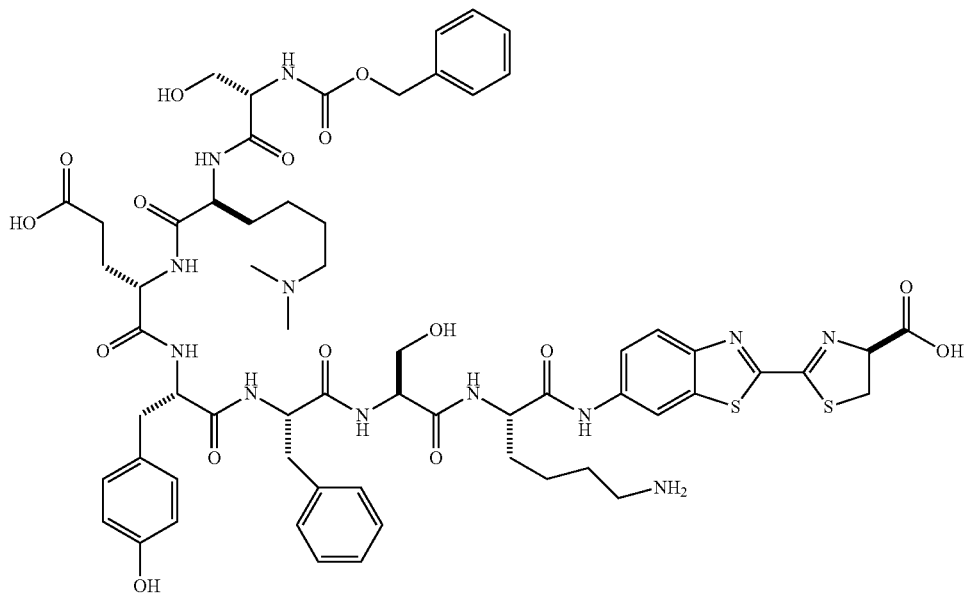

(18)

This compound will be synthesized in a manner similar to compound 14.

Boc-Lys(Me₂)GlyLeuGlyLys(Me₂)GlyGlyAlaLys-aminoluciferin (SEQ ID NO:18) (19)

(19)

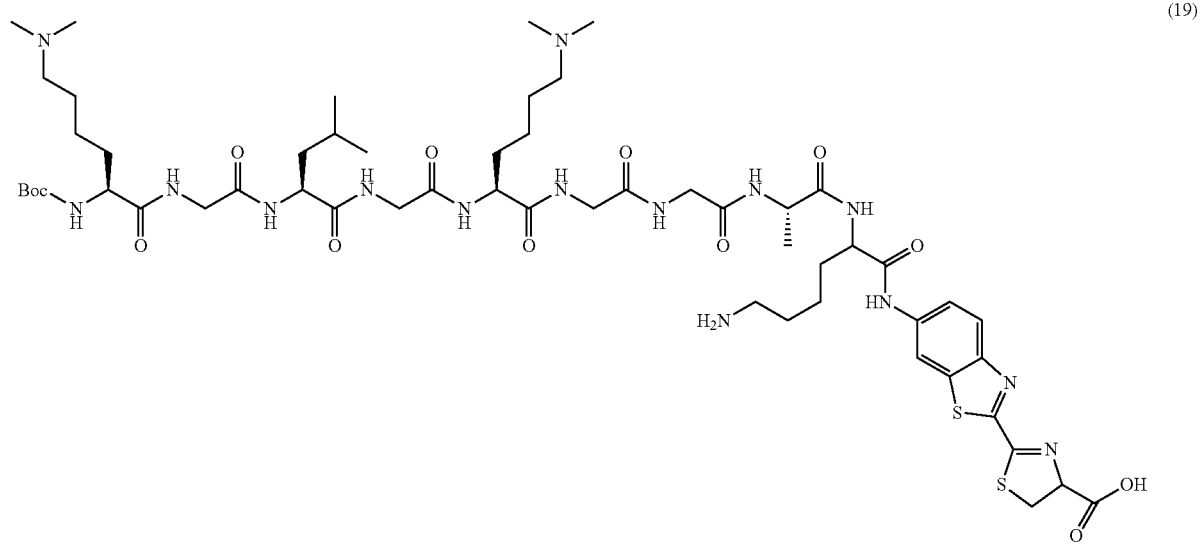 [SMILES: CC(C)C[C@H](NC(=O)CNC(=O)[C@H](CCCCN(C)C)NC(=O)OC(C)(C)C)C(=O)NCC(=O)N[C@@H](CCCCN(C)C)C(=O)NCC(=O)NCC(=O)N[C@@H](C)C(=O)NC(CCCCN)C(=O)Nc1ccc2nc(C3=NC(C(=O)O)CS3)sc2c1]

This compound will be synthesized in a manner similar to compound 15.

Example 5

Determining the Potency of a SIRT1 Inhibitor

Figure 2:
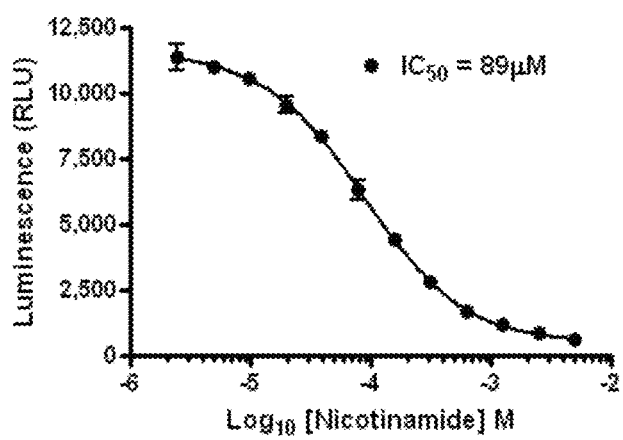
FIG. 2 depicts results of an inhibition assay of the enzyme SIRT1 (Biomol) using the inhibitor nicotinamide using an exemplary method of the invention.

Nicotinamide was serially diluted two-fold in SIRT-Glo™ Buffer (Promega), and 50 µL added to a white, 96-well plate. 50 µL of SIRT-Gl o™ Buffer was added to wells which were to be "uninhibited" and "no enzyme" controls. SIRT1 enzyme (Biomol) was diluted in SIRT-Glo™ Buffer and added in an equal volume (50 µL) to all wells. The plate was then placed on an orbital shaker at 500-700 rpm to ensure homogeneity in the samples and incubated at room temperature for 30 minutes. Following incubation, 100 µL of Compound 1 (solubilized as in Example 6) was added to all wells. The plate was incubated for 15-30 minutes at room temperature with shaken to allow the reactions to reach enzyme steady state, and luminescence detected on a BMG Labtech PolarStar Optima luminometer. FIG. 2 shows the IC₅₀ value of nicotinamide as determined by Prism™ software from GraphPad.

Example 6

Assay for Histone Deacetylase Activity Using Lys-C Endopeptidase 10 mg of Compound 1 was solubilized by first adding ½ volume (518 µL) DMSO followed by ½ volume (518 µL) water to a create 10 mM solution. A partial deacetylase reagent was prepared by combining Luciferin Detection Reagent (Promega; prepared by rehydrating a lyophilized luciferin cake with 9.8 mL buffer) and 200 µL 10 mM compound 1 (200 µM final concentration). The reagent was incubated in a 37° C. water bath for 1 hour to burn off any residual aminoluciferin that may have co-purified with compound 1. Lys-C (500 ng/mL) was serially diluted two-fold into 100 µL of buffer containing HeLa Nuclear Extract (diluted 1:3000) and added to a 96-well plate. The partial deacetylase reagent was equilibrated to room temperature, and 100 µL added to the wells of the plate. The plate was briefly mixed on an orbital shaker, and luminescence detected using a BMG PolarStar luminometer.

All patents, publications and references cited herein are hereby fully incorporated by reference. In case of conflict between the present disclosure and incorporated patents, publications and references, the present disclosure should control.

---

The invention claimed is:

1. A method of detecting the activity of a histone deacetylase enzyme, comprising:

a) reacting a compound according to formula (I):

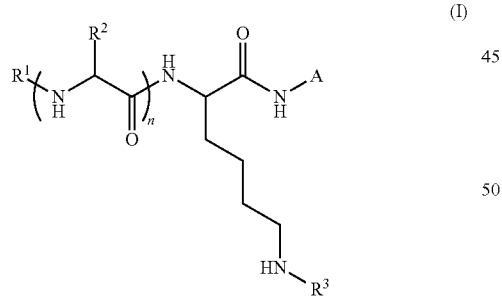

wherein:
A is

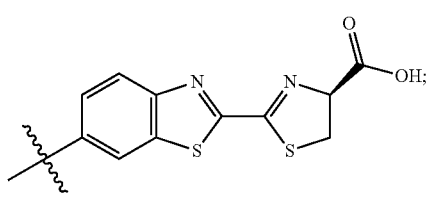 [SMILES: *c1ccc2nc(C3=N[C@@H](C(=O)O)CS3)sc2c1]

$R^1$ is selected from H, an amino protecting group and an amino blocking group;

n is an integer from 1 to 20;

each $R^2$ is independently an amino acid side chain, wherein at least one $R^2$ is selected from $-CH_2-CH_2-CH_2-CH_2-NR^{4a}R^{4b}$, $-CH_2-CH_2-CH_2-CH_2-N^+R^{4a}R^{4b}R^{4c}$ and $-CH_2-CH_2-CH_2-NH-C(=NR^{5a})NR^{5b}R^{5c}$;

$R^3$ is acyl;

each $R^{4a}$ is independently selected from hydrogen, alkyl and aryl;

each $R^{4b}$ is independently selected from alkyl and aryl;

each $R^{4c}$ is independently selected from hydrogen, alkyl and aryl;

each $R^{5a}$ is independently selected from hydrogen, alkyl and aryl;

each $R^{5b}$ is independently selected from alkyl and aryl; and each $R^{5c}$ is independently selected from hydrogen, alkyl and aryl, wherein when $R^2$ is $-CH_2-CH_2-CH_2-CH_2-N^+R^{4a}R^{4b}R^{4c}$, the compound further comprises a counteranion with a histone deacetylase enzyme and an endopeptidase that recognizes basic amino acids, under conditions sufficient to allow the histone deacetylase enzyme to react with the compound of formula (I) to form a product, and the endopeptidase to react with the product to release a compound A-$NH_2$; and b) detecting the compound A-NH$_2$.

2. The method of claim 1, further comprising correlating the detection of the compound A-NH$_2$ with the activity of the histone deacetylase enzyme.

3. The method of claim 2, wherein the activity of the histone deacetylase enzyme is quantified.

4. The method of claim 1, wherein the endopeptidase does not react with the compound of formula (I).

5. The method of claim 1, wherein the product has the following formula (II):

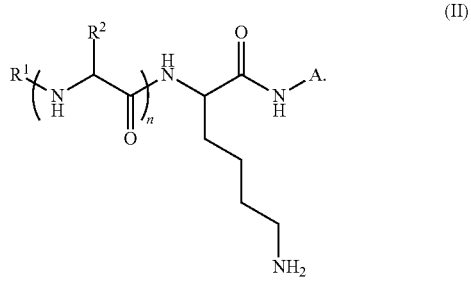

(II)

6. The method of claim 1, wherein the value of n and the identity of each R2 moiety are chosen to confer specificity for the histone deacetylase enzyme.

7. The method of claim 1, wherein the endopeptidase that recognizes basic amino acids is trypsin, Lys-C or Arg-C.

8. The method of claim 1, wherein R$^1$ is an amino protecting group or an amino blocking group selected from the group consisting of 9-fluorenylmethyloxycarbonyl (Fmoc), carbobenzyloxy (Cbz), tertbutyloxy (Boc), acetyl and succinyl.

9. The method of claim 1, wherein n is 2, 3, 4 or 5.

10. The method of claim 1, wherein at least one R$^2$ is selected from —CH$_2$—CH$_2$—CH$_2$—CH$_2$—NH—CH$_3$, —CH$_2$—CH$_2$—CH$_2$—CH$_2$—N(CH$_3$)$_2$, —CH$_2$—CH$_2$—CH$_2$—CH$_2$—N(CH$_3$)$_3$ and —CH$_2$—CH$_2$—CH$_2$—NH—C(=NH)NHCH$_3$.

11. The method of claim 1, wherein R$^3$ is selected from acetyl and trifluoroacetyl.

12. The method of claim 1, wherein the compound is selected from:

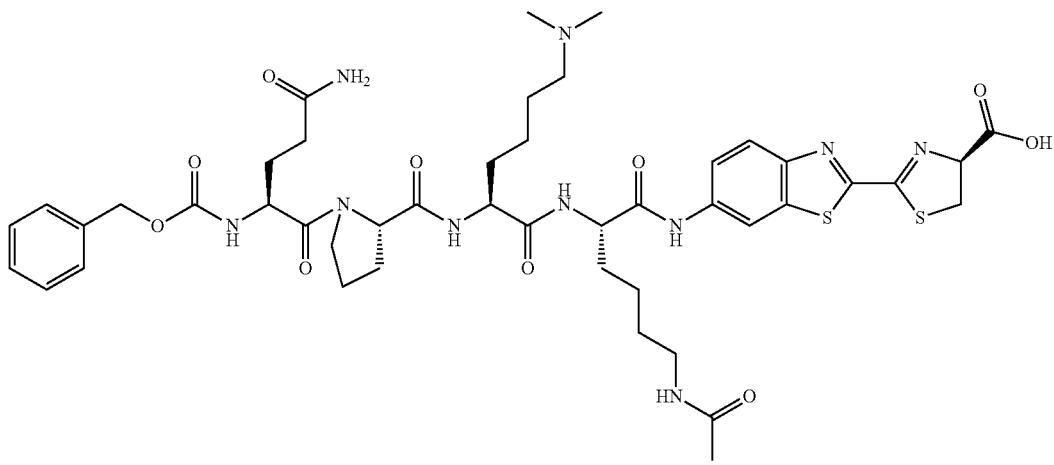

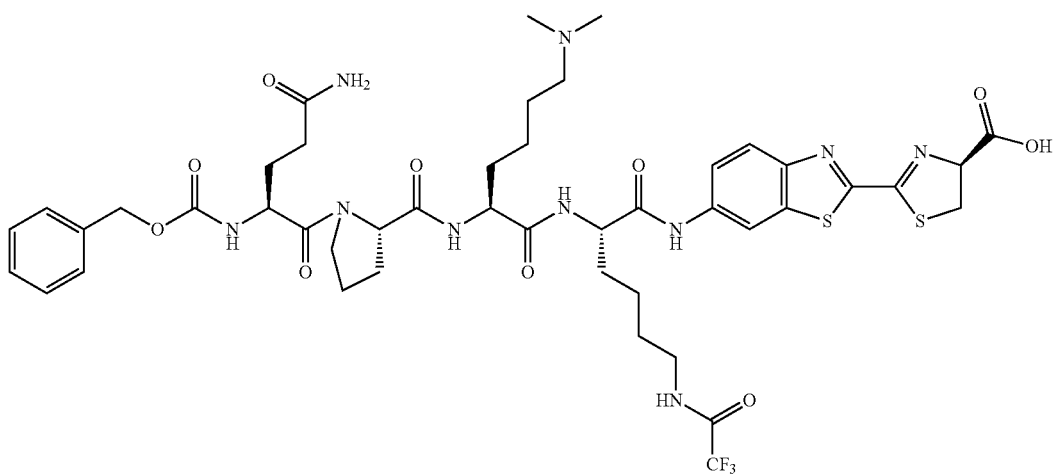

-continued
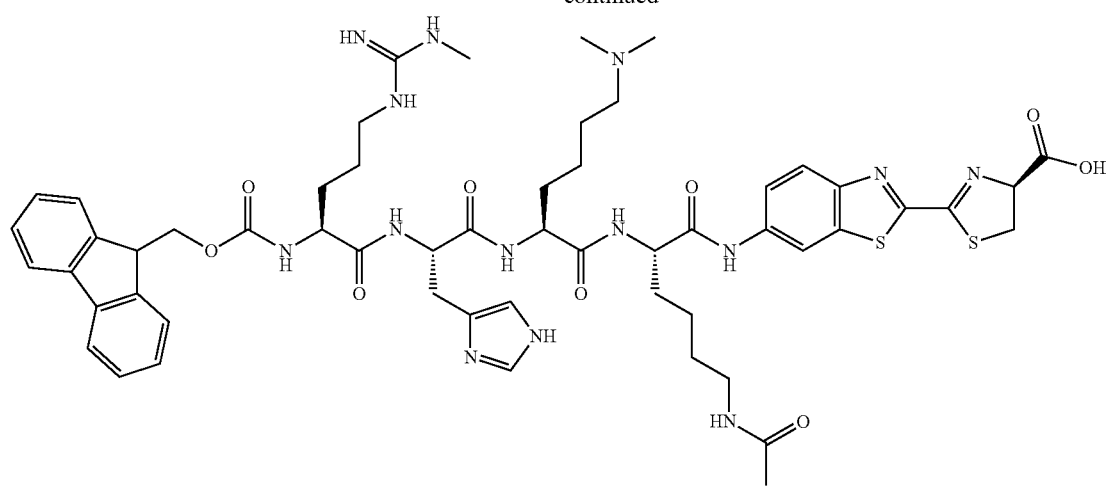
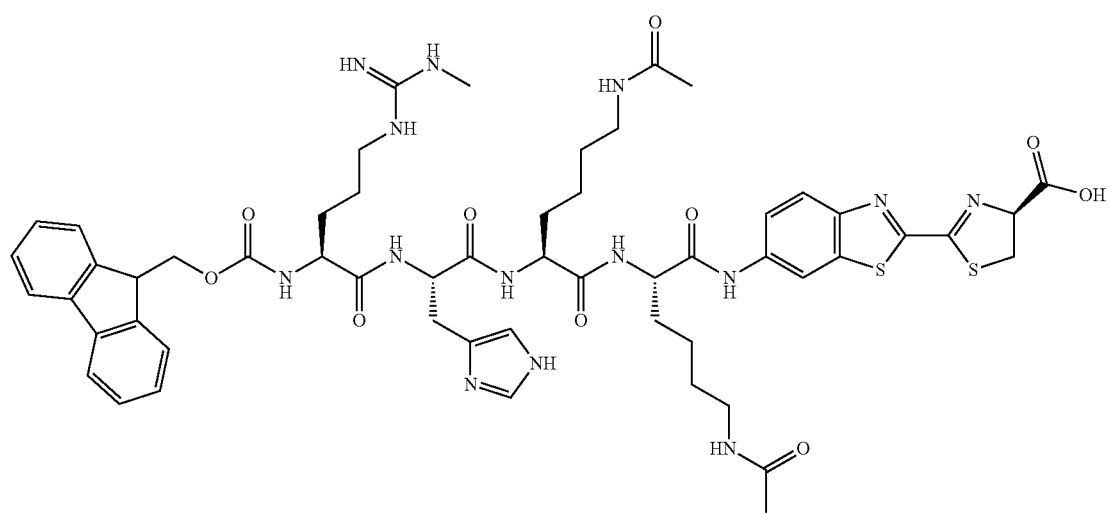
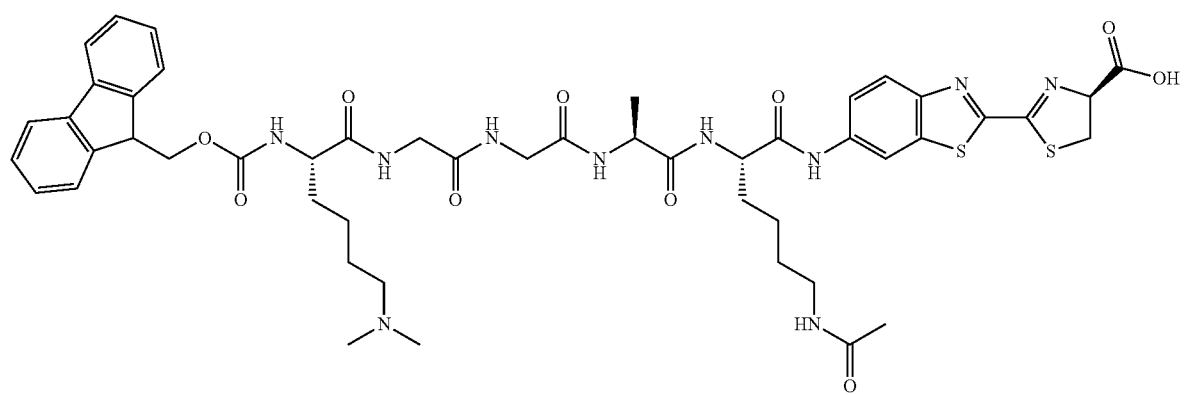

-continued
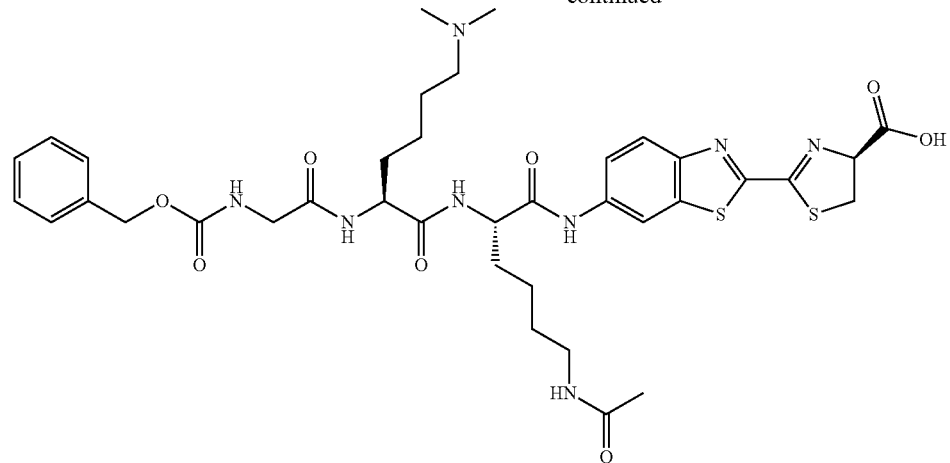
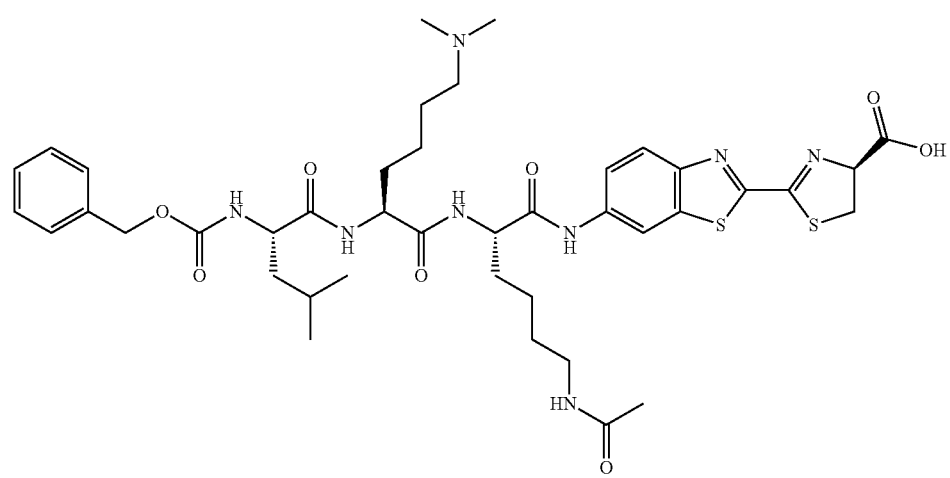
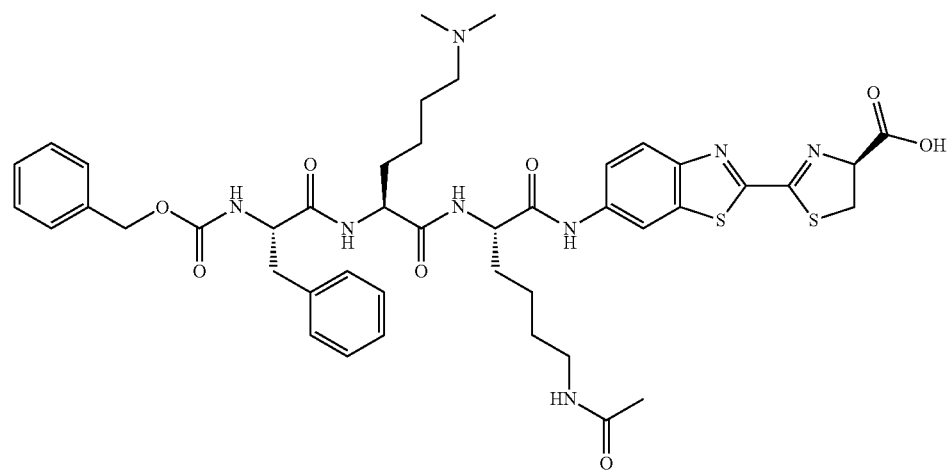

-continued
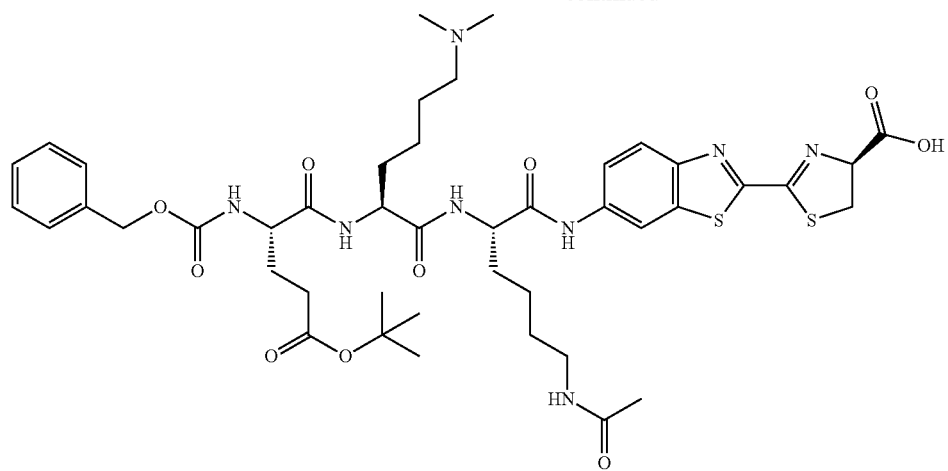
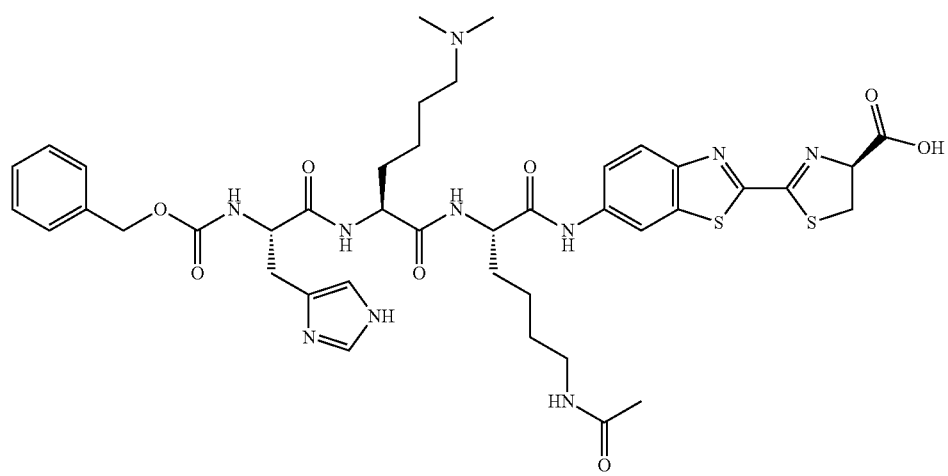
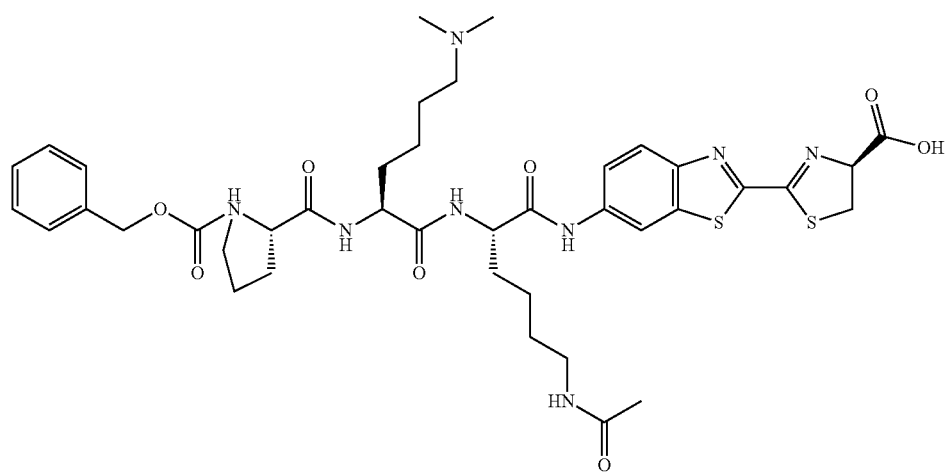

-continued
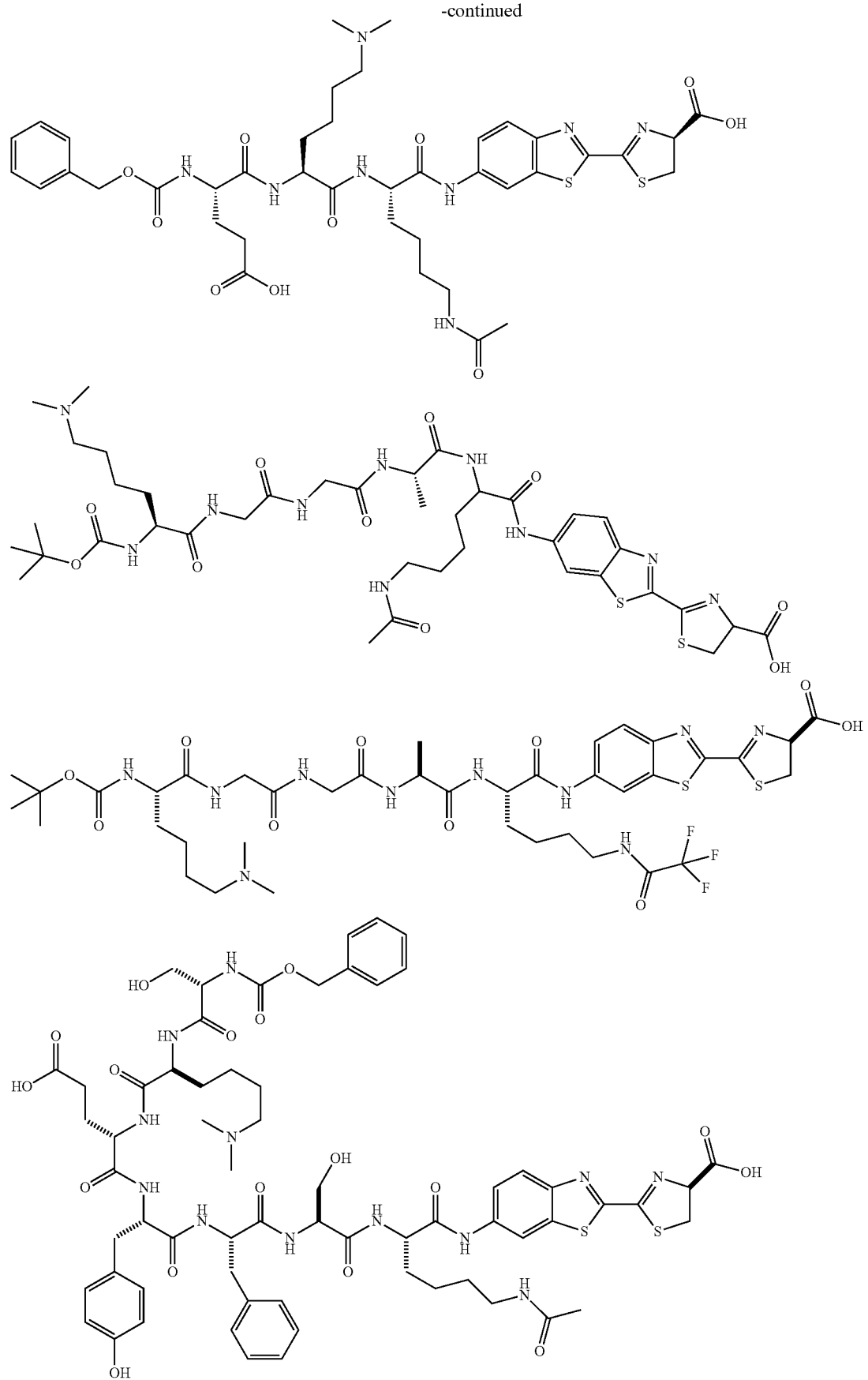

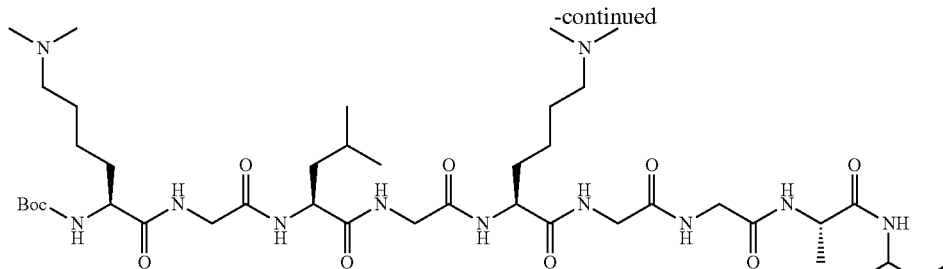
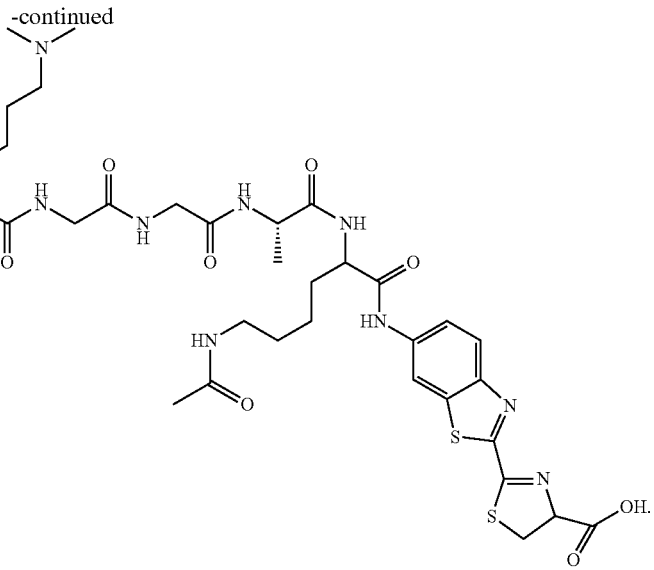

13. A method of detecting the activity of a target enzyme, comprising:

a) reacting a compound according to formula (I):

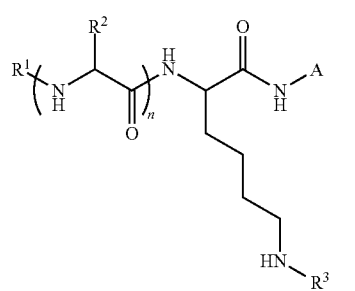

wherein:

A is

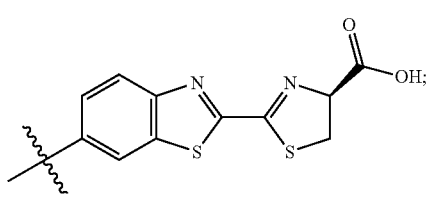 [SMILES: *c1ccc2nc(C3=N[C@@H](C(=O)O)CS3)sc2c1]

$R^1$ is selected from H, an amino protecting group and an amino blocking group;

n is an integer from 1 to 20;

each $R^2$ is independently an amino acid side chain, wherein at least one $R^2$ is selected from $CH_2$—$CH_2$—$CH_2$—$CH_2$—$NR^{4a}R^{4b}$, —$CH_2$—$CH_2$—$CH_2$—$CH_2$—$N^+R^{4a}R^{4b}R^{4c}$ and —$CH_2$—$CH_2$—$CH_2$—$NH$—$C(=NR^{5a})NR^{5b}R^{5c}$;

$R^3$ is H or acyl;

each $R^{4a}$ is independently selected from hydrogen, alkyl and aryl;

each $R^{4b}$ is independently selected from alkyl and aryl;

each $R^{4c}$ is independently selected from hydrogen, alkyl and aryl;

each $R^{5a}$ is independently selected from hydrogen, alkyl and aryl;

each $R^{5b}$ is independently selected from alkyl and aryl; and each $R^{5c}$ is independently selected from hydrogen, alkyl and aryl, wherein when $R^2$ is —$CH_2$—$CH_2$—$CH_2$—$CH_2$—$N^+R^{4a}R^{4b}R^{4c}$, the compound further comprises a counteranion wherein the compound comprises at least one blocked arginine or lysine residue;

with a target enzyme and an endopeptidase that recognizes basic amino acids, wherein the reaction results in the formation of a compound A-$NH_2$; and b) detecting the compound A-$NH_2$;

wherein the target enzyme is a histone deacetylase or histone acetyltransferase enzyme.

* * * * *